United States Patent
Feng et al.

(10) Patent No.: US 9,890,253 B2
(45) Date of Patent: Feb. 13, 2018

(54) CROSS-LINKED AMINOSILOXANE POLYMER AND METHOD OF FORMING

(71) Applicant: Dow Corning Corporation, Midland, MI (US)

(72) Inventors: Qian Feng, Midland, MI (US); Patrick J. Fryfogle, Midland, MI (US); Bethany K. Johnson, Midland, MI (US); Zhi Li, Midland, MI (US); Kimmai Thi Nguyen, Midland, MI (US); Ryan Christopher Thomas, Freeland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 15/311,664

(22) PCT Filed: May 20, 2015

(86) PCT No.: PCT/US2015/031768
§ 371 (c)(1),
(2) Date: Nov. 16, 2016

(87) PCT Pub. No.: WO2015/179513
PCT Pub. Date: Nov. 26, 2015

(65) Prior Publication Data
US 2017/0096534 A1    Apr. 6, 2017
US 2017/0355824 A9    Dec. 14, 2017

Related U.S. Application Data

(60) Provisional application No. 62/001,415, filed on May 21, 2014, provisional application No. 62/001,421, (Continued)

(51) Int. Cl.
*C07F 7/02* (2006.01)
*C08G 77/388* (2006.01)
(Continued)

(52) U.S. Cl.
CPC ........... *C08G 77/388* (2013.01); *C08G 77/26* (2013.01); *C08K 5/1539* (2013.01)

(58) Field of Classification Search
CPC ..... C08G 77/388; C08G 77/26; C08K 5/1538
(Continued)

(56) References Cited

U.S. PATENT DOCUMENTS 2,798,053 A    7/1957    Brown
3,597,268 A    8/1971    Smith
(Continued)

FOREIGN PATENT DOCUMENTS

AU    B5243590    4/1990
CA    2274040 A1    11/2000
(Continued)

OTHER PUBLICATIONS

PCT/US2015/031768 International Search Report dated Sep. 10, 2015, 3 pages
(Continued)

*Primary Examiner* — Sudhakar Katakam
*Assistant Examiner* — Kofi Adzamli
(74) *Attorney, Agent, or Firm* — Warner Norcross & Judd LLP

(57) ABSTRACT

A cross-linked aminosiloxane polymer includes a first siloxane backbone, a second siloxane backbone, and at least one intramolecular structure cross-linking a silicon atom of the first siloxane backbone and a silicon atom of the second siloxane backbone. The intramolecular structure has the chemical structure: (I) In Formula (I), X is chosen from the following groups; (II); (III); or (IV). In groups (II), (III), and (IV), each R is independently a $C_1$-$C_{10}$ hydrocarbon group. Each $R^1$ is independently a $C_1$-$C_{10}$ hydrocarbon group. Each $R^2$ is independently a hydrogen atom, OH, a $C_1$-$C_{12}$ hydrocarbon group, a phenyl group, $R'(OR'')_m$, or R'OH. Each of R' and R" is independently an alkyl group and "m" is 1 to 3. Moreover, "a" is 0 or 1. The cross-linked aminosiloxane polymer can be formed by the method of this disclosure.

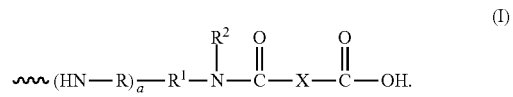

(I)

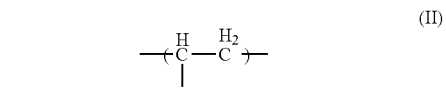

(II)

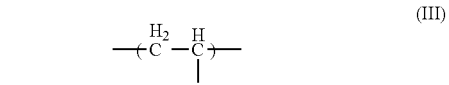

(III); or

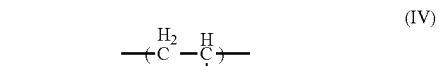

(IV)

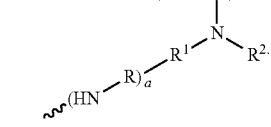

20 Claims, 5 Drawing Sheets

Related U.S. Application Data filed on May 21, 2014, provisional application No. 62/001,427, filed on May 21, 2014.

(51) Int. Cl.
*C08G 77/26* (2006.01)
*C08K 5/1539* (2006.01)

(58) Field of Classification Search
USPC .......................................................... 556/410
See application file for complete search history.

(56) References Cited

U.S. PATENT DOCUMENTS

| | | |
|---|---|---|
| 3,958,581 A | 5/1976 | Abegg et al. |
| 3,962,418 A | 6/1976 | Birkofer |
| 4,009,256 A | 2/1977 | Nowak, Jr. et al. |
| 4,070,152 A | 1/1978 | Pentz |
| 4,250,108 A | 2/1981 | Bouillon et al. |
| 4,290,974 A | 9/1981 | Bouillon et al. |
| 4,304,730 A | 12/1981 | Bouillon et al. |
| 4,311,626 A | 1/1982 | Ona et al. |
| 4,323,549 A | 4/1982 | Bouillon et al. |
| 4,327,031 A | 4/1982 | Bouillon et al. |
| 4,330,488 A | 5/1982 | Bouillon et al. |
| 4,387,089 A | 6/1983 | De Polo |
| 4,406,880 A | 9/1983 | Bouillon et al. |
| 4,489,057 A | 12/1984 | Welters et al. |
| 4,562,067 A | 12/1985 | Hopp et al. |
| 4,585,597 A | 4/1986 | Lang et al. |
| 4,704,272 A | 11/1987 | Oh et al. |
| 4,741,855 A | 5/1988 | Grote et al. |
| 4,775,526 A | 10/1988 | Lang et al. |
| 4,788,006 A | 11/1988 | Bolich, Jr. et al. |
| 5,391,400 A | 2/1995 | Yang |
| 5,399,652 A | 3/1995 | Bindl et al. |
| 5,643,557 A | 7/1997 | Eteve et al. |
| 5,690,915 A | 11/1997 | Eteve et al. |
| 5,690,917 A | 11/1997 | Eteve et al. |
| 5,695,747 A | 12/1997 | Forestier et al. |
| 5,708,070 A | 6/1998 | Joffre et al. |
| 5,762,912 A | 6/1998 | Eteve |
| 5,763,540 A | 6/1998 | Nakata et al. |
| 5,788,955 A | 8/1998 | Eteve et al. |
| 5,795,565 A | 8/1998 | Eteve et al. |
| 5,919,441 A | 7/1999 | Mendolia et al. |
| 5,976,557 A | 11/1999 | Friedrich et al. |
| 5,981,680 A | 11/1999 | Petroff et al. |
| 6,001,946 A | 12/1999 | Waldman et al. |
| 6,013,682 A | 1/2000 | Dalle et al. |
| 6,051,216 A | 4/2000 | Barr et al. |
| 6,124,490 A | 9/2000 | Gormley et al. |
| 6,171,516 B1 | 1/2001 | Inuzuka et al. |
| 6,248,855 B1 | 6/2001 | Dalle et al. |
| 6,277,445 B1 | 8/2001 | Hasegawa et al. |
| 6,329,462 B1 | 12/2001 | Hale et al. |
| 6,379,751 B1 | 4/2002 | Schafer et al. |
| 6,437,042 B2 | 8/2002 | Kobayashi et al. |
| RE38,116 E | 5/2003 | Petroff et al. |
| 7,078,026 B2 | 7/2006 | Ferrari et al. |
| 8,455,603 B2 | 6/2013 | Ferenz et al. |
| 8,580,241 B2 | 11/2013 | Moriya |
| 8,940,282 B2 | 1/2015 | Seng et al. |
| 2003/0068348 A1 | 4/2003 | Ferrari et al. |
| 2003/0072730 A1 | 4/2003 | Tournilhac |
| 2003/0170188 A1 | 9/2003 | Ferrari et al. |
| 2003/0235553 A1 | 12/2003 | Lu et al. |
| 2004/0180032 A1 | 9/2004 | Manelski et al. |
| 2006/0269506 A1 | 11/2006 | De Caire et al. |
| 2008/0254076 A1 | 10/2008 | Ferrari et al. |
| 2009/0183320 A1 | 7/2009 | Benabdillah |
| 2011/0039087 A1 | 2/2011 | Cauvin et al. |
| 2011/0052523 A1 | 3/2011 | Moriya et al. |
| 2011/0230633 A1 | 9/2011 | Ferenz et al. |
| 2012/0149930 A1* | 6/2012 | Moriya ................. A61K 8/898 556/419 |
| 2017/0000722 A1 | 1/2017 | Feng et al. |

FOREIGN PATENT DOCUMENTS

| | | |
|---|---|---|
| EP | 0114607 A1 | 1/1983 |
| EP | 0487404 A1 | 5/1992 |
| EP | 0518772 A1 | 12/1992 |
| EP | 0518773 A1 | 12/1992 |
| EP | 0678292 A1 | 10/1995 |
| EP | 1266647 A1 | 12/2002 |
| EP | 1266648 A1 | 12/2002 |
| EP | 1266653 A1 | 12/2002 |
| FR | 2236515 A1 | 2/1975 |
| FR | 2282426 A2 | 3/1976 |
| FR | 2326405 A1 | 4/1977 |
| FR | 2430938 A1 | 2/1980 |
| FR | 2440933 A1 | 6/1980 |
| FR | 2592380 A1 | 7/1987 |
| FR | 2645148 A1 | 10/1990 |
| JP | H05320348 A | 12/1993 |
| JP | H07179479 A | 7/1995 |
| JP | H0790205 B2 | 10/1995 |
| JP | H08127657 A | 5/1996 |
| JP | H10158150 A | 6/1998 |
| JP | 2000186149 A | 7/2000 |
| JP | 2001234071 A | 8/2001 |
| JP | 2001240679 A | 9/2001 |
| JP | 2004182680 A | 7/2004 |
| JP | 2006169130 A | 6/2006 |
| JP | 2007016156 A | 1/2007 |
| JP | 2007284359 A | 11/2007 |
| JP | 201146657 A | 3/2011 |
| JP | 2011511830 A | 4/2011 |
| JP | 201382819 A | 5/2013 |
| WO | WO9522311 A1 | 8/1995 |
| WO | WO9522331 A1 | 8/1995 |
| WO | WO9840553 A1 | 9/1998 |
| WO | WO03101412 A2 | 12/2003 |
| WO | WO03105789 A1 | 12/2003 |
| WO | WO03105801 A1 | 12/2003 |
| WO | WO03106614 A2 | 12/2003 |
| WO | WO2004000247 A1 | 12/2003 |
| WO | WO2004054523 A1 | 7/2004 |
| WO | WO2004054524 A1 | 7/2004 |
| WO | WO2004060101 A2 | 7/2004 |
| WO | WO2004060271 A2 | 7/2004 |
| WO | WO2004060276 A2 | 7/2004 |
| WO | WO2015179011 A1 | 11/2015 |
| WO | WO2015179512 A1 | 11/2015 |
| WO | WO2015179513 A1 | 11/2015 |
| WO | WO2016014127 A1 | 1/2016 |
| WO | WO2016014128 A1 | 1/2016 |

OTHER PUBLICATIONS

English language abstract and machine translation for FR2282426 (A2) extracted from http://worldwide.espacenet.com database on Aug. 26, 2016, 15 pages.

English language abstract and machine translation for FR2645148 (A1) extracted from http://worldwide.espacenet.com database on Aug. 31, 2016, 31 pages.

PCT/US2015/031167 International Search Report dated Sep. 10, 2015, 3 pages.

PCT/US2015/020640 International Search Report dated Jun. 3, 2015, 4 pages.

English language abstract and machine translation for JPH08127657 (A) extracted from http://worldwide.espacenet.com database on Dec. 4, 2017, 39 pages.

English language abstract and machine translation for JPH07179479 (A) extracted from http://worldwide.espacenet.com database on Dec. 12, 2017, 14 pages.

English language abstract and machine translation for JP2004182680 (A) extracted from http://worldwide.espacenet.com database on Dec. 12, 2017, 16 pages.

(56) References Cited

OTHER PUBLICATIONS

English language abstract and machine translation for JP2006169130 (A) extracted from http://worldwide.espacenet.com database on Dec. 12, 2017, 14 pages.

English language abstract and machine translation for JP2007016156 (A) extracted from http://worldwide.espacenet.com database on Dec. 12, 2017, 22 pages.

English language abstract and machine translation for JP2007284359 (A) extracted from http://worldwide.espacenet.com database on Dec. 12, 2017, 21 pages.

English language abstract and machine translation for JPH0790205 (B2) extracted from http://worldwide.espacenet.com database on Dec. 12, 2017, 12 pages.

* cited by examiner

CROSS-LINKED AMINOSILOXANE POLYMER AND METHOD OF FORMING

CROSS-REFERENCE TO RELATED APPLICATIONS

This application is the National Stage of International Application No. PCT/US2015/031768 filed on 20 May 2015, which claims priority to and all advantages of U.S. Appl. No. 62/001,415 filed on 21 May 2014, U.S. Appl. No. 62/001,421 filed on 21 May 2014, and U.S. Appl. No. 62/001,427 filed on 21 May 2014, the contents of which are hereby incorporated by reference.

FIELD OF THE INVENTION

This disclosure generally relates to a cross-linked aminosiloxane polymer that includes an intramolecular structure having a particular chemical formula. This disclosure also provides a method of forming the cross-linked aminosiloxane polymer.

BACKGROUND OF THE INVENTION

The desire to have hair retain a particular shape is widely held. The two methodologies of accomplishing this are permanent chemical alteration of the hair or temporary alteration. A temporary alteration is one which can be removed by water or by shampooing. This has generally been accomplished by means of applying a composition to dampened hair after shampooing and/or conditioning and prior to drying and/or styling. The materials used to provide setting benefits are resins or gums and are sold in the form of mousses, gels, lotions, or sprays. However, these materials tend to increase difficulty with combing the hair, degrade hair feel, and can be difficult to work with. Accordingly, there remains an opportunity for improvement.

BRIEF SUMMARY OF THE INVENTION

This disclosure provides a cross-linked aminosiloxane polymer including a first siloxane backbone, a second siloxane backbone, and at least one intramolecular structure. The intramolecular structure cross-links a silicon atom of the first siloxane backbone and a silicon atom of the second siloxane backbone. The intramolecular structure has the chemical structure:

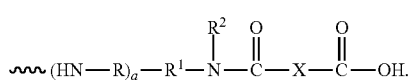

In structure (I), X is chosen from the following groups:

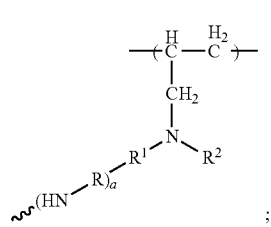

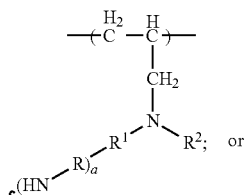

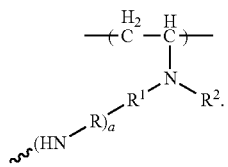

In groups (II), (III), and (IV), each R is independently a $C_1$-$C_{10}$ hydrocarbon group. Each $R^1$ is independently a $C_1$-$C_{10}$ hydrocarbon group. Each $R^2$ is independently a hydrogen atom, OH, a $C_1$-$C_{12}$ hydrocarbon group, a phenyl group, R'(OR")$_m$, or R'OH. Each of R' and R" is independently an alkyl group and "m" is 1 to 3. Moreover, "a" is 0 or 1. This disclosure also provides a method of forming the aminosiloxane polymer.

BRIEF DESCRIPTION OF THE DRAWINGS

Other advantages of the present disclosure will be readily appreciated, as the same becomes better understood by reference to the following detailed description when considered in connection with the accompanying drawings wherein.

DETAILED DESCRIPTION

Figure 1:
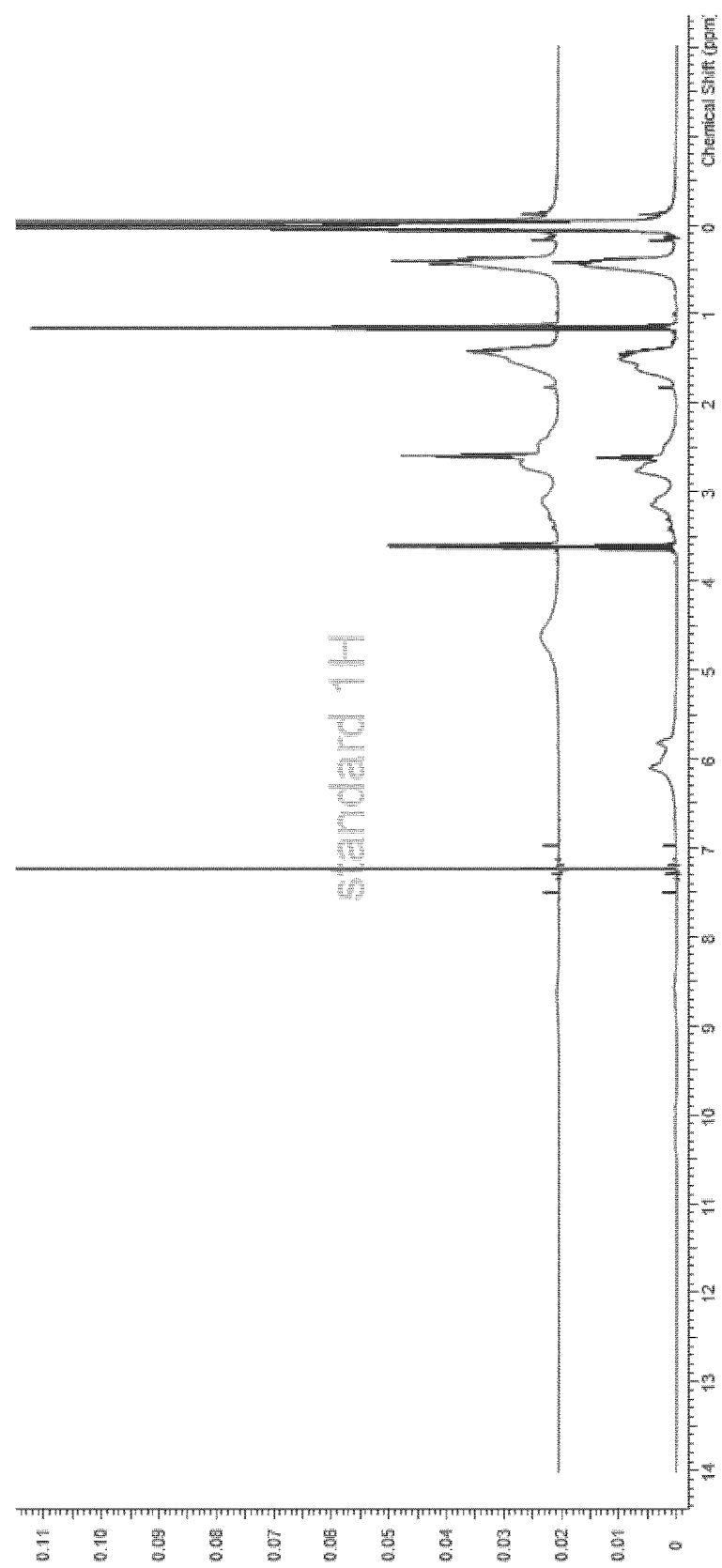
FIG. 1 is an NMR spectrograph of Example 1A (lowermost line) and Example 1B (uppermost line)

This disclosure provides a cross-linked aminosiloxane polymer, which may hereinafter be described as the aminosiloxane polymer. The aminosiloxane polymer includes a first siloxane backbone, a second siloxane backbone, and at least one intramolecular structure. The intramolecular structure cross-links a silicon atom of the first siloxane backbone and a silicon atom of the second siloxane backbone. The terminology "cross-linked" describes that the first siloxane backbone and the second siloxane backbone is connected, in at least one place, by the intramolecular structure. Typically, the aminosiloxane polymer has two or more points of cross-linking or connection between the first and second siloxane backbones (i.e., with one or more intramolecular structures extending between the first and second siloxane backbones). In various embodiments, the aminosiloxane polymer includes 2-100, 5-100, 5-95, 10-90, 15-85, 20-80, 25-75, 30-70, 35-65, 40-60, 45-55, or 50-55, alternatively 1, 2, 3, 4, 5, 6, 7, 8, 9, or 10, points of connection (or cross-linking) between the first and second siloxane backbones. All values and ranges of values therebetween are also expressly contemplated in various non-limiting embodiments.

First and Second Siloxane Backbones:

The first and second siloxane backbones are not particularly limited so long as they each include at least one silicon atom. Each may independently include any M, D, T, and Q units. The symbols M, D, T, and Q represent the functionality of structural units of polyorganosiloxanes. M represents the monofunctional unit $R^0_3SiO_{1/2}$. D represents the difunctional unit $R^0_2SiO_{2/2}$. T represents the trifunctional unit $R^0SiO_{3/2}$. Q represents the tetrafunctional unit $SiO_{4/2}$. Generic structural formulas of these units are shown below:

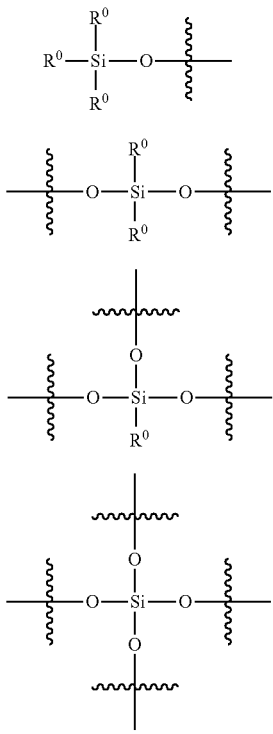

[M]

[D]

[T]

[Q]

In these structures/formulae, each $R^0$ may be any hydrocarbon, aromatic, aliphatic, alkyl, alkenyl, or alkynl group. Similarly, the siloxane backbones are not particularly limited in molecular weight or viscosity and may be a fluid, gum, gel, etc.

In various embodiments, the first siloxane backbone has the chemical structure:

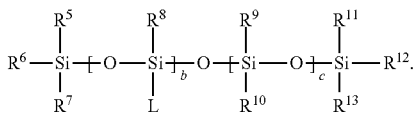

(A)

In structure (A), each of $R^5$-$R^{13}$ is independently a hydrogen atom, a $C_1$-$C_{12}$ hydrocarbon group, a $C_2$-$C_{30}$ alkenyl group, a $C_6$-$C_{12}$ aromatic group, $R'(OR'')_m$, or a polyalkyleneoxy group. Each of R' and R" is independently an alkyl group and "m" is 1-3. In one embodiment, R" is methyl. Moreover, "b" is from 1-100 and "c" is from 1-3,000. "L" is the intramolecular structure.

In various embodiments, "m" is 1, 2, or 3. In certain embodiments, "b" can be from 1-100, 5-95, 10-90, 15-85, 20-80, 25-75, 30-70, 35-65, 40-60, 45-55, or 50-55. In certain embodiments, "c" can be from 1-3,000, 1-2,500, 1-2,000, 1-1,500, 1-1,000, 1-500, or 1-100, alternatively from 200-600, 250-550, 300-500, 350-450, or 400-450. All values and ranges of values therebetween, and all combinations of these values, are hereby expressly contemplated in various non-limiting embodiments.

In various embodiments, the second siloxane backbone has the chemical structure:

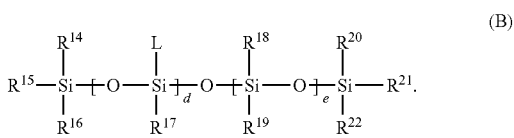

(B)

In structure (B), each of $R^{14}$-$R^{22}$ is independently a hydrogen atom, a $C_1$-$C_{12}$ hydrocarbon group, a $C_2$-$C_{30}$ alkenyl group, a $C_6$-$C_{12}$ aromatic group, $R'(OR'')_m$, or a polyalkyleneoxy group. Each of R' and R" is independently an alkyl group and "m" is 1-3. In one embodiment, R" is methyl. Moreover, "d" is from 1-100 and "e" is from 1-3,000. "L" is the intramolecular structure. The first and the second siloxane backbones can be the same or different from each other.

In various embodiments, "m" is 1, 2, or 3. In certain embodiments, "d" can be from 1-100, 5-95, 10-90, 15-85, 20-80, 25-75, 30-70, 35-65, 40-60, 45-55, or 50-55. In certain embodiments, "e" can be from 1-3,000, 1-2,500, 1-2,000, 1-1,500, 1-1,000, 1-500, or 1-100, alternatively from 200-600, 250-550, 300-500, 350-450, or 400-450. All values and ranges of values therebetween, and all combinations of these values, are hereby expressly contemplated in various non-limiting embodiments.

In various embodiments, at least one or each of $R^5$-$R^{13}$ and/or $R^{14}$-$R^{22}$ (collectively referred to as "$R^5$-$R^{22}$") is independently a hydrogen atom. Alternatively, at least one or each of $R^5$-$R^{13}$ and/or $R^{14}$-$R^{22}$ can independently be a $C_1$-$C_{12}$ hydrocarbon group, e.g. methyl, ethyl, or propyl, or any hydrocarbon group having up to 12 carbon atoms. More specifically, the hydrocarbon group can have 1, 2, 3, 4, 5, 6, 7, 8, 9, 10, 11, or 12 carbon atoms or any range of values therebetween. Hydrocarbons can include saturated hydrocarbons, unsaturated hydrocarbons having one or more double or triple bonds between carbon atoms, cycloalkanes having one or more carbon rings to which hydrogen atoms are attached, or aromatic hydrocarbons. In certain embodiments, at least one of $R^5$-$R^{22}$ is a methyl group.

In other embodiments, at least one or each of $R^5$-$R^{13}$ and/or $R^{14}$-$R^{22}$ can independently be a $C_2$-$C_{30}$ alkenyl group and have any number of carbon atoms or range of carbon atoms between 2 and 30, alternatively can independently be a $C_2$-$C_{12}$ alkenyl group and have any number of carbon atoms or range of carbon atoms between 2 and 12. In further embodiments, at least one or each of $R^5$-$R^{13}$ and/or $R^{14}$-$R^{22}$ can independently be a $C_6$-$C_{12}$ aromatic group and have any number of carbon atoms or range of carbon atoms between 6 and 12. In certain embodiments, at least one of $R^5$-$R^{22}$ is a phenyl group.

In still other embodiments, at least one or each of $R^5$-$R^{13}$ and/or $R^{14}$-$R^{22}$ can independently be $R'(OR'')_m$ where each of R' and R" is independently an alkyl group and "m" is 1-3. This alkyl group may be, for example, methyl, ethyl, or propyl, or any hydrocarbon group having up to 12 carbon atoms, but is not limited in such a way. In further embodiments, at least one of $R^5$-$R^{22}$ is R'OH where R' is an alkyl group. Examples of suitable alkyl groups are described above.

In still other embodiments, at least one or each of $R^5$-$R^{13}$ and/or $R^{14}$-$R^{22}$ can independently be a polyalkyleneoxy group. Polyalkyleneoxy groups may be alternatively described as alkylene oxide (AO) groups, such as an ethylene oxide (EO) groups, propylene oxide (PO) groups, butylene oxide (BO) groups, etc., or combinations thereof. In still other embodiments, examples of suitable AO groups that can be utilized include, but are not limited to, EO groups, PO groups, BO groups, amylene oxide groups, mixtures thereof, AO-tetrahydrofuran mixtures, epihalohydrins, and aralkylene styrenes, and combinations thereof. The structures of these compounds are known in the art. All combinations of the aforementioned groups for the first and second siloxane backbones are hereby expressly contemplated in various non-limiting embodiments.

It is contemplated that any one or more of $R^5$-$R^{13}$ may be substituted for any one or more of $R^{14}$-$R^{22}$. In other non-limiting embodiments, any one or more of $R^5$-$R^{13}$ may be the same as any one or more of $R^{14}$-$R^{22}$. In additional non-limiting embodiments, wherever any one or more of $R^5$-$R^{13}$ is shown herein, any one or more of $R^{14}$-$R^{22}$ may be substituted.

Intramolecular Structure:

The aminosiloxane polymer also includes at least one intramolecular structure cross-linking a silicon atom of the first siloxane backbone and a silicon atom of the second siloxane backbone, as introduced above. The intramolecular structure has the chemical structure:

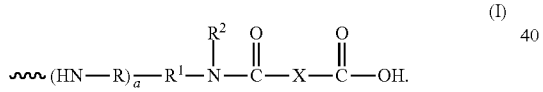

(I)

In structure (I), X is chosen from the following groups:

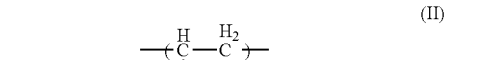

(II)

(III)

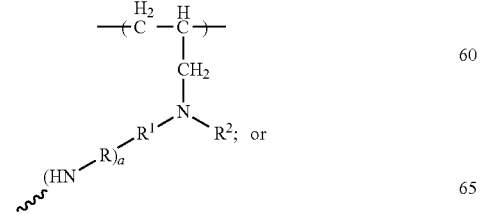

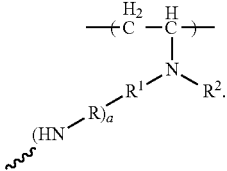

(IV)

In groups (II), (Ill), and (IV), each R is independently a $C_1$-$C_{10}$ hydrocarbon group. Each $R^1$ is independently a $C_1$-$C_{10}$ hydrocarbon group. Each $R^2$ is independently a hydrogen atom, OH, a $C_1$-$C_{12}$ hydrocarbon group, a phenyl group, R'(OR")$_m$, or R'OH. Each of R' and R" is independently an alkyl group and "m" is 1-3. Moreover, "a" is 0 or 1.

More specifically, and in various embodiments, the intramolecular structure can have the following chemical structures:

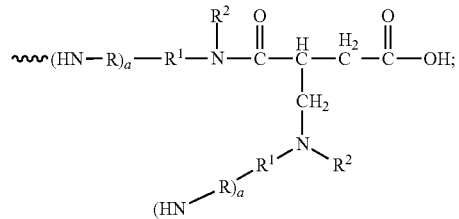

(V)

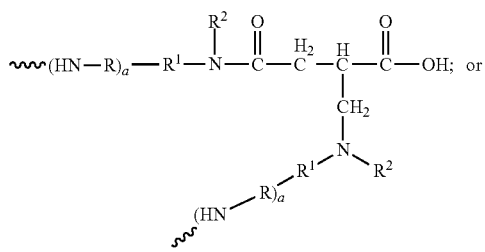

(VI)

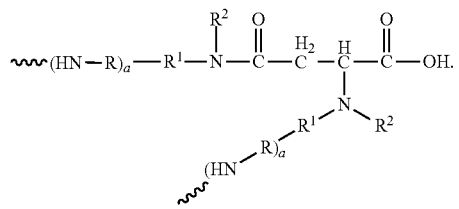

(VII)

In groups (V), (VI), and (VII), each of R, $R^1$, $R^2$, and "a" are as described above.

In various embodiments, each R is independently a $C_1$-$C_{10}$ hydrocarbon group, e.g. methyl, ethyl, or propyl, or any hydrocarbon group having up to 10 carbon atoms, for example, as described above. R can have 1, 2, 3, 4, 5, 6, 7, 8, 9, or 10 carbon atoms or any range of values therebetween. In certain embodiments, at least one or each of R is independently a $C_1$-C6 hydrocarbon group. Moreover, "a" is 0 or 1, such that (HN—R) is optional, i.e., if "a" is 0, then (R—NH) is not present. In one embodiment, "a" is 1. In another embodiment, "a" is 0.

$R^1$ may be any of the groups described above relative to R and may be independently chosen from R, i.e., R and $R^1$ may be the same or different from one another. In certain embodiments, at least one or each of $R^1$ is independently a $C_1$-$C_6$ hydrocarbon group.

In various embodiments, at least one or both of $R^2$ is a hydrogen atom. In additional embodiments, at least one or both of $R^2$ is OH. In other embodiments, at least one or both of $R^2$ is independently a $C_1$-$C_{12}$ hydrocarbon group that can have 1, 2, 3, 4, 5, 6, 7, 8, 9, 10, 11, or 12, carbon atoms or any range of values therebetween. The hydrocarbon group may be as described above. In certain embodiments, at least one or each of $R^2$ is independently a $C_1$-C6 hydrocarbon group. In still other embodiments, at least one or both of $R^2$ is a phenyl group. In other embodiments, at least one or both of $R^2$ is independently $R'(OR'')_m$. Each of R' and R" is independently an alkyl group that may be any described above or may be different. Moreover, "m" is 1, 2, or 3. In still other embodiments, at least one or both of $R^2$ is independently R'OH. R' is independently an alkyl group that may be any described above or may be different.

Reaction Product:

In one embodiment, the aminosiloxane polymer includes, or is the reaction product of, a polyorganosiloxane having an amino group and maleic anhydride and/or itaconic anhydride. Each of the maleic anhydride and itaconic anhydride may also be referred to generally as an alkenyl cyclic anhydride. In another embodiment, the aminosiloxane polymer includes, or is the reaction product of, a polyorganosiloxane having an amino group and a polyorganosiloxane that has an α,β-unsaturated carboxy acid amide group, which itself may result from the reaction of the polyorganosiloxane having the amino group and the maleic anhydride and/or the itaconic anhydride. The reaction of the polyorganosiloxane having the amino group and the maleic anhydride and/or the itaconic anhydride may proceed to form the aminosiloxane polymer but while doing may form the polyorganosiloxane that has an α,β-unsaturated carboxy acid amide group as an intermediate that itself reacts with another molecule of the starting polyorganosiloxane having the amino group.

Polyorganosiloxane Having an Amino Group:

The polyorganosiloxane having the amino group may be any in the art. For example, the polyorganosiloxane may include any M, D, T, and Q units, as described above.

In various embodiments, the polyorganosiloxane has the following chemical formula:

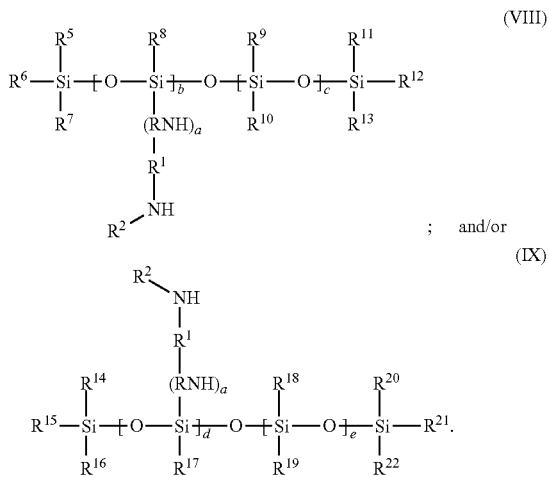

In Formulas (VIII) and (IX), each of R, $R^1$, $R^2$, $R^5$-$R^{22}$, "a", "b", "c", "d", and "e" are as described above. Mixtures or combinations may also be used.

The polyorganosiloxane that has the α,β-unsaturated carboxy acid amide group is not particularly limited. The α,β-unsaturation may be relative to an amide group or to a carboxylic acid group. In one embodiment, this polyorganosiloxane is described as having an α,β-unsaturated carboxylic acid amide group.

In various embodiments, the polyorganosiloxane that has the α,β-unsaturated carboxy acid amide group has the chemical formula:

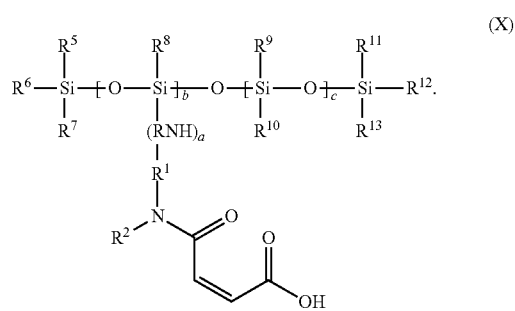

In Formula (X), each of R, $R^1$, $R^2$, $R^5$-$R^{13}$, "a", "b", and "c" are as described above.

In other embodiments, the polyorganosiloxane that has the α,β-unsaturated carboxy acid amide group is the reaction product of a second polyorganosiloxane and maleic anhydride, wherein the second polyorganosiloxane has an amino group. The second polyorganosiloxane having the amino group may be the same as the polyorganosiloxane described above or may be different. In other embodiments, the second polyorganosiloxane having the amino group has the formula as described above.

Maleic anhydride has the following formula and structure:

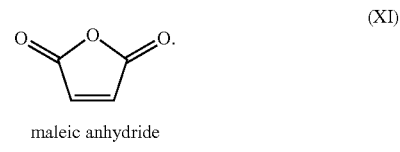

maleic anhydride

Chemical Formula:
$C_4H_2O_3$

Due to the symmetry of maleic anhydride, typically only one major product will be formed in the aforementioned reactions as shown in the reaction scheme below:

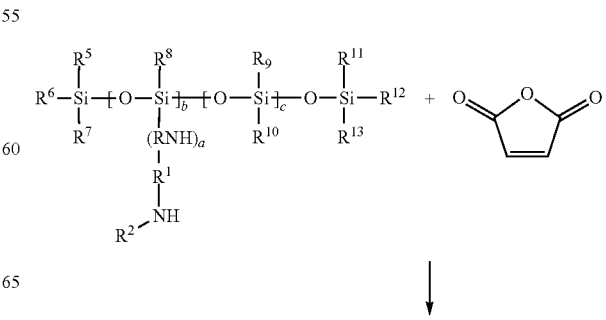

-continued

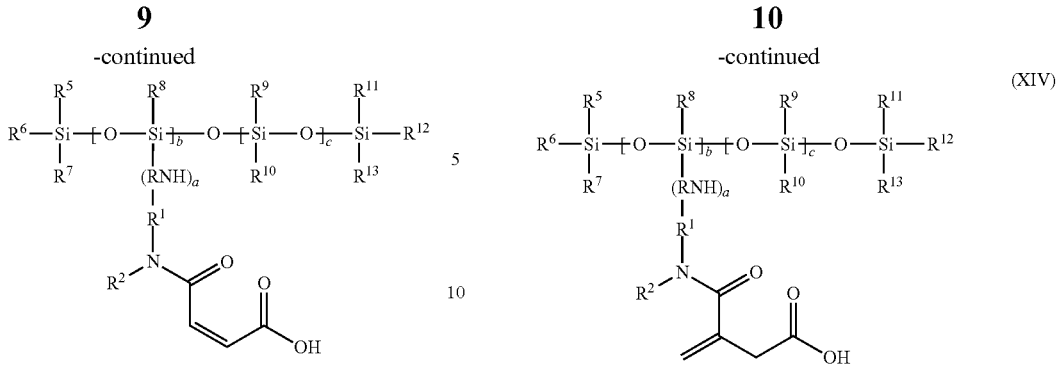

In this reaction scheme, each of R, $R^1$, $R^2$, $R^5$-$R^{13}$, "a", "b", and "c" are as described above.

In other embodiments, the polyorganosiloxane that has the α,β-unsaturated carboxy acid amide group is the reaction product of the second polyorganosiloxane and itaconic anhydride, wherein the second polyorganosiloxane has an amino group. The second polyorganosiloxane having the amino group may be the same as the polyorganosiloxane described above or may be different. In other embodiments, the second polyorganosiloxane having the amino group has the formula as described above.

Itaconic anhydride has the following formula and structure:

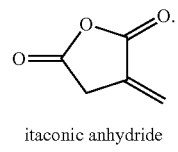

itaconic anhydride

Chemical Formula:
$C_5H_4O_3$

When utilizing the asymmetrical itaconic anhydride, various major products may be formed, as shown in non-limiting examples below. Accordingly, the polyorganosiloxane that has the α,β-unsaturated carboxy acid amide group may have the following structures and may be formed using the following reaction scheme:

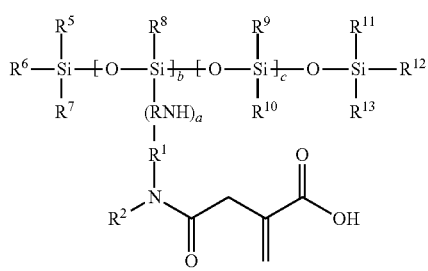

In this reaction scheme, each of R, $R^1$, $R^2$, $R^5$-$R^{13}$, "a", "b", and "c" are as described above.

In each of the aforementioned groups, structures, formulas, and/or reaction schemes, where a cis- or trans-isomer/moiety may be illustrated, the other isomer/moiety is also contemplated (not shown). Moreover, where an acidic or basic component may be illustrated, it may also be coordinated, i.e., in a salt form (not shown) that is contemplated for purposes of this disclosure. For example, acidic groups may be coordinated with a surrounding amine to form an acid-based ionic salt.

In still other embodiments, the maleic anhydride and/or the itaconic anhydride reacts in an amount of from about 0.01-0.5, 0.1-0.4, or 0.01-0.33, moles per 1 mole of the amino group of the second organopolysiloxane, or any value or range of values therebetween.

Cross-Linked Aminosiloxane Polymer:

The aminosiloxane polymer itself is not particularly limited except as described herein in various embodiments. For example, the weight or number average molecular weight of the aminosiloxane polymer is not particularly limited. In various embodiments, the aminosiloxane polymer has a weight average molecular weight of from about 310-300,000, 10,000-100,000, or 15,000-60,000, g/mol. Similarly, the degree of polymerization ("Dp") of the first and second siloxane backbones of the aminosiloxane polymer is not particularly limited. In various embodiments, the Dp is from about 1-3,000, 100-1,000, or 200-600. Even further, the ratio of "b" and "c", and/or of "d" and "e", of the siloxane backbones is not particularly limited. In various embodiments, the ratio is from about 0.01-1, 0.01-0.5, or 0.01-0.2. Moreover, the viscosity of the aminosiloxane polymer is not particularly limited. In various embodiments, the viscosity is from about 10-100,000, 100-10,000, or 500-5,000, cP as measured using a Brookfield viscometer at 25° C.

In various embodiments, the cross-linked aminosiloxane has the chemical structure:

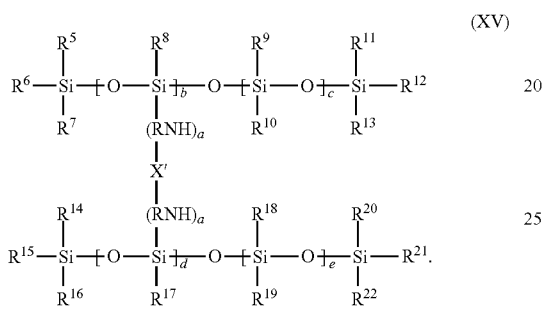
(XV)

In structure (XV), X' is chosen from the following three groups:

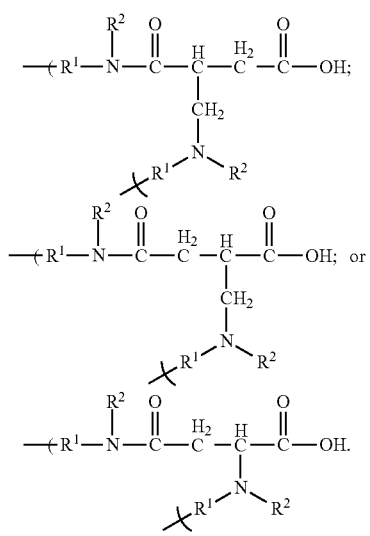

Moreover, each of R, $R^1$, $R^2$, $R^5$-$R^{22}$, "a", "b", "c", "d", and "e" are as described above.

Method of Forming the Aminosiloxane Polymer:

This disclosure also provides a method of forming the cross-linked aminosiloxane polymer. The method includes the steps of providing the polyorganosiloxane having the amino group, providing the maleic anhydride and/or the itaconic anhydride, and combining the maleic anhydride and/or itaconic anhydride and the polyorganosiloxane having the amino group to form the cross-linked aminosiloxane polymer.

This reaction may occur via the following reaction schemes, but is not limited as such.

Reaction Scheme One:

Polyorganosiloxane having the amine group + itaconic anhydride

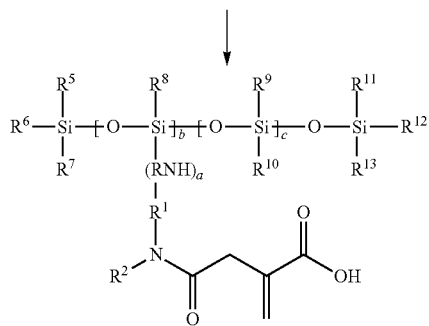

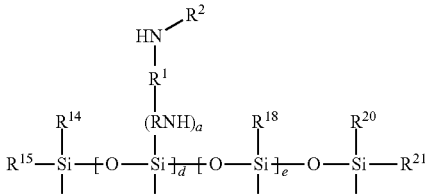

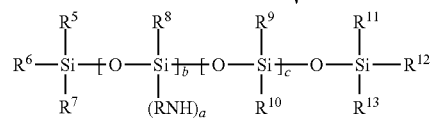

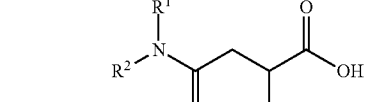

Each of R, $R^1$, $R^2$, $R^5$-$R^{22}$, "a", "b", "c", "d", and "e" are as described above.

Reaction Scheme Two:

Polyorganosiloxane having the amine group + itaconic anhydride

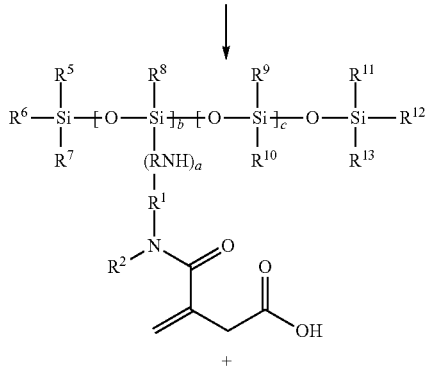

-continued

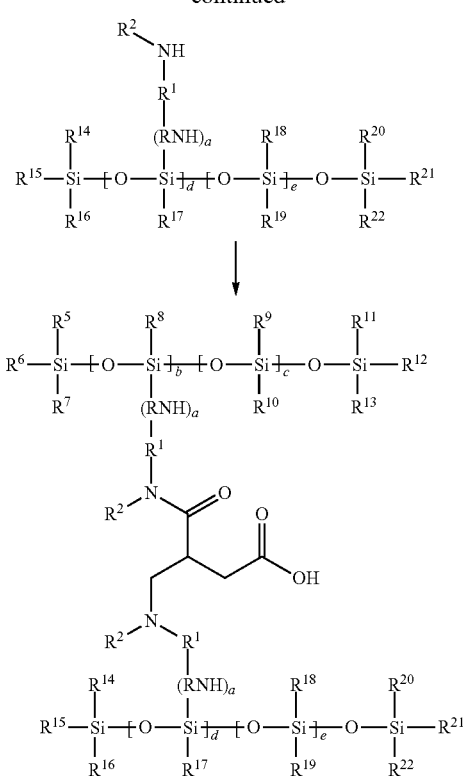

Each of R, $R^1$, $R^2$, $R^5$-$R^{22}$, "a", "b", "c", "d", and "e" are as described above.

Reaction Scheme Three:

Polyorganosiloxane having the amine group + maleic anhydride

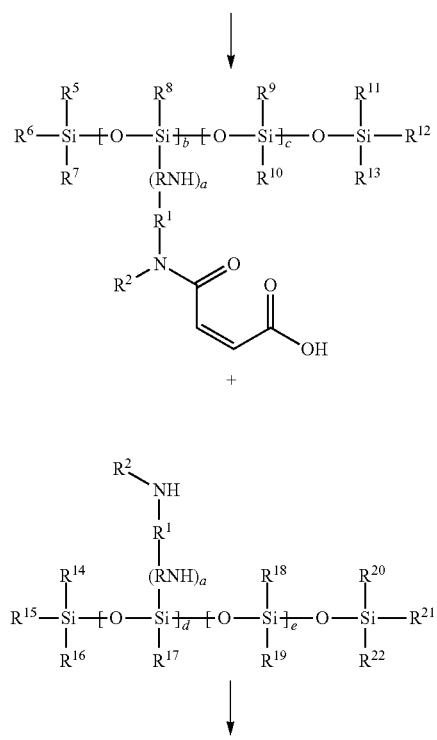

-continued

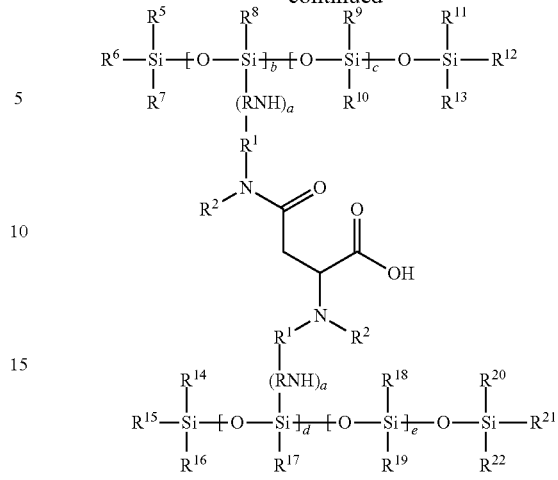

Each of R, $R^1$, $R^2$, $R^5$-$R^{22}$, "a", "b", "c", "d", and "e" are as described above.

In each of the aforementioned groups, structures, formulas, and/or reaction schemes, where a cis- or trans-isomer/moiety may be illustrated, the other isomer/moiety is also contemplated (not shown). Moreover, where an acidic or basic component may be illustrated, it may also be coordinated, i.e., in a salt form (not shown) that is contemplated for purposes of this disclosure. For example, acidic groups may be coordinated with a surrounding amine to form an acid-based ionic salt.

Each of the steps of providing may be further defined as any known in the art. For example, each of the aforementioned components may be provided in a vessel, reactor, etc., and may be provided in a batch-wise or continuous manner and at any appropriate temperature, pressure, rate, and/or amount, as is understood by those of skill in the art.

In one embodiment, the step of providing the maleic anhydride and/or the itaconic anhydride is further defined as providing the maleic anhydride in the absence of the itaconic anhydride. In another embodiment, the step of providing the maleic anhydride and/or the itaconic anhydride is further defined as providing the itaconic anhydride in the absence of the maleic anhydride.

When utilized, the maleic anhydride typically reacts with the polyorganosiloxane having the amino group in an amount of from about 0.01-0.5, 0.01-0.45, or 0.1-0.4, moles per mole of amino group. Moreover, when utilized, the itaconic anhydride typically reacts with the polyorganosiloxane having the amino group in an amount of from about 0.01-0.5, 0.01-0.45, or 0.1-0.4, moles per mole of amino group. Even further, if both the maleic anhydride and the itaconic anhydride are utilized, the total amount of the maleic anhydride and the itaconic anhydride that are utilized is typically of from about 0.01-0.5, 0.01-0.45, or 0.1-0.4, moles per mole of amino group. However, this disclosure is not limited to these amounts. All values and ranges of values therebetween the aforementioned values are hereby expressly contemplated in various non-limiting embodiments.

In other embodiments, the method further includes the step of heating the polyorganosiloxane having the amino group and the maleic anhydride and/or itaconic anhydride to a temperature of from about −20 to 100, 0-100, 20-100, 40-100, 60-100, 65-95, 70-90, 75-85, or 80-85, ° C. In a specific embodiment, the step of heating involves a temperature of from about 40-90° C. In still other embodiments, the step of providing the maleic anhydride and/or itaconic anhydride is further defined as providing about 0.01-0.5, 0.01-0.45, 0.1-0.4, or 0.01-0.33, moles of the maleic anhydride and/or itaconic anhydride per 1 mole of the amino group of the polyorganosiloxane. All values and ranges of values therebetween the aforementioned values are hereby expressly contemplated in various non-limiting embodiments.

Additional Embodiments

In various embodiments, the aminosiloxane polymer is a gel. In other embodiments, the aminosiloxane polymer is an elastomer. In still other embodiments, the aminosiloxane polymer is a solid. This disclosure also provides a film including the aminosiloxane polymer. The film may be of any dimensions relative to length, width, and thickness. Typically, the film is formed using the aminosiloxane polymer. For example, the aminosiloxane polymer may be poured onto a substrate and then dried to form the film. The substrate may be any in the art including plastic, wood, glass, polymers, metal, human skin, human hair, fabric, textiles, and the like.

In other embodiments, this disclosure provides a use of the aminosiloxane polymer or the film as a cosmetic ingredient. Alternatively, this disclosure provides a use of the aminosiloxane polymer or the film as a fabric treating agent. Alternatively, this disclosure provides a use of the aminosiloxane polymer or the film as a fiber treating agent or composition. Still further, this disclosure provides a cosmetic composition including the aminosiloxane polymer or the film. This disclosure also provides a hair care composition including the aminosiloxane polymer or the film. This disclosure further provides a fabric treating composition including the aminosiloxane polymer or the film. This disclosure further provides a fiber treating composition including the aminosiloxane polymer or the film.

The film and/or aminosiloxane polymer of the instant disclosure can be useful in many applications, for example in personal care applications, such as on hair, skin, mucous membrane or teeth. In many of these applications, the film and/or aminosiloxane polymer is lubricious and improves properties of skin creams, skin care lotions, moisturizers, facial treatments, such as acne or wrinkle removers, personal and facial cleansers, bath oils, perfumes, fragrances, colognes, sachets, sunscreens, pre-shave and after shave lotions, shaving soaps and shaving lathers. The film and/or aminosiloxane polymer can likewise be used in hair shampoos, hair conditioners, hair sprays, mousses, permanents, depilatories, and cuticle coats, for example to provide styling and conditioning benefits. In cosmetics, the film and/or aminosiloxane polymer may function as a leveling and spreading agent for pigment in make-ups, color cosmetics, foundations, blushes, lipsticks, eye liners, mascaras, oil removers, color cosmetic removers and powders. The film and/or aminosiloxane polymer may also be useful as a delivery system for oil and water soluble substances, such as vitamins, organic sunscreens, ceramides, pharmaceuticals and the like. When compounded into sticks, gels, lotions aerosols and roll-ons, the film and/or aminosiloxane polymer may impart a dry silky-smooth payout. The film and/or aminosiloxane polymer may also be mixed with deposition polymers, surfactants, detergents, antibacterials, anti-dandruffs, foam boosters, proteins, moisturizing agents, suspending agents, opacifiers, perfumes, coloring agents, plant extracts, polymers, and other conventional care ingredients. In one embodiment, the film and/or aminosiloxane polymer is included in a water based composition that is chosen from the group of cosmetic compositions, fabric treating compositions, hair care compositions, fiber care compositions, and combinations thereof. The film and/or aminosiloxane polymer may be used in personal care products in amounts of from about 0.01-50, or 0.1-25, weight percent of a personal care product.

The film and/or aminosiloxane polymer may also be useful for numerous other applications, such as textile fiber treatment, leather lubrication, fabric softening, release agents, water based coatings, oil drag reduction, particularly in crude oil pipelines, lubrication, facilitation of cutting cellulose materials, and in many other areas where silicones are conventionally used. The film and/or aminosiloxane polymer may also be used to reduce oil drag. The film and/or aminosiloxane polymer can also be used in antimicrobial applications, in preservatives, deodorants, wound dressings, and dentifrices, and as a catalyst in organic synthesis reactions. Further, the film and/or aminosiloxane polymer can be used in filters and solar cells.

This disclosure also provides a personal care composition, which may also be described as a personal care product composition. The personal care composition includes the aminosiloxane polymer. The personal care composition may be in the form of a cream, a gel, a powder, a paste, or a freely pourable liquid. Generally, such compositions can be prepared at room temperature if no solid materials at room temperature are present in the compositions, using simple propeller mixers, Brookfield counter-rotating mixers, or homogenizing mixers. No special equipment or processing conditions are typically required. Depending on the type of form made, the method of preparation will be different, but such methods are well known in the art.

The personal care composition may be functional with respect to the portion of the body to which it is applied, cosmetic, therapeutic, or some combination thereof. Conventional examples of such products include, but are not limited to, antiperspirants and deodorants, skin care creams, skin care lotions, moisturizers, facial treatments, such as acne or wrinkle removers, personal and facial cleansers, bath oils, perfumes, colognes, sachets, sunscreens, pre-shave and after-shave lotions, shaving soaps, and shaving lathers, hair shampoos, hair conditioners, hair colorants, hair relaxants, hair sprays, mousses, gels, permanents, depilatories, and cuticle coats, make-ups, color cosmetics, foundations, concealers, blushes, lipsticks, eyeliners, mascara, oil removers, color cosmetic removers, and powders, medicament creams, pastes or sprays including anti-acne, dental hygienic, antibiotic, healing promotive, nutritive and the like, which may be preventative and/or therapeutic. In general, the personal care composition may be formulated with a carrier that permits application in any conventional form, including but not limited to liquids, rinses, lotions, creams, pastes, gels, foams, mousses, ointments, sprays, aerosols, soaps, sticks, soft solids, solid gels, and gels. Suitable carriers are appreciated in the art.

The personal care composition can be used in or for a variety of personal, household, and healthcare applications. In particular, the aminosiloxane polymer and/or personal care compositions of the present disclosure may be used in the personal care products as described in U.S. Pat. Nos. 6,051,216, 5,919,441, 5,981,680; WO 2004/060271 and WO 2004/060101; in sunscreen compositions as described in WO 2004/060276; in cosmetic compositions also containing film-forming resins, as described in WO 03/105801; in the cosmetic compositions as described in US Pat. App. Pub. Nos. 2003/0235553, 2003/0072730 and 2003/0170188, in EP Pat. Nos. 1,266,647, 1,266,648, and 1,266,653, in WO 03/105789, WO 2004/000247 and WO 03/106614; as additional agents to those described in WO 2004/054523; in long wearing cosmetic compositions as described in US Pat. App. Pub. No. 2004/0180032; and/or in transparent or translucent care and/or make up compositions as described in WO 2004/054524, all of which are expressly incorporated herein by reference in various non-limiting embodiments.

The personal care composition and/or aminosiloxane polymer can be used by the standard methods, such as applying them to the human body, e.g. skin or hair, using applicators, brushes, applying by hand, pouring them and/or possibly rubbing or massaging the composition onto or into the body. Removal methods, for example for color cosmetics are also well known standard methods, including washing, wiping, peeling and the like. For use on the skin, the personal care composition and/or aminosiloxane polymer may be used in a conventional manner for example for conditioning the skin. An effective amount of the personal care composition and/or aminosiloxane polymer may be applied to the skin. Such effective amounts generally are from about 1-3 mg/cm$^2$. Application to the skin typically includes working the personal care composition and/or aminosiloxane polymer into the skin. This method for applying to the skin typically includes the steps of contacting the skin with the personal care composition and/or aminosiloxane polymer in an effective amount and then rubbing the personal care composition and/or aminosiloxane polymer into the skin. These steps can be repeated as many times as desired to achieve the desired benefit.

Use of the personal care composition and/or aminosiloxane polymer on hair may use a conventional manner for conditioning hair. An effective amount of the personal care composition and/or aminosiloxane polymer for conditioning hair is applied to the hair. Such effective amounts generally are from about 1-50, or 1-20, g. Application to the hair typically includes working the personal care composition and/or aminosiloxane polymer through the hair such that most or all of the hair is contacted with the personal care composition and/or aminosiloxane polymer. This method for conditioning the hair typically includes the steps of applying an effective amount of the personal care composition and/or aminosiloxane polymer to the hair, and then working the personal care composition and/or aminosiloxane polymer through the hair. These steps can be repeated as many times as desired to achieve the desired conditioning benefit.

Non-limiting examples of additives which may be formulated into the personal care composition, cosmetic composition, fabric treating composition, hair care composition, film and/or aminosiloxane polymer, or any other compositions described above, include, but are not limited to, additional silicones, anti-oxidants, cleansing agents, colorants, additional conditioning agents, deposition agents, electrolytes, emollients and oils, exfoliating agents, foam boosting agents, fragrances, humectants, occlusive agents, pediculicides, pH control agents, pigments, preservatives, biocides, other solvents, stabilizers, sun-screening agents, suspending agents, tanning agents, other surfactants, thickeners, vitamins, botanicals, waxes, rheology-modifying agents, anti-dandruff, anti-acne, anti-cane and wound healing-promotion agents.

The personal care composition, such as a shampoo or cleanser, film, aminosiloxane polymer, and/or any other composition described above, may include at least one anionic detersive surfactant. This can be any of the well-known anionic detersive surfactants typically used in shampoo formulations. These anionic detersive surfactants can function as cleansing agents and foaming agents in the shampoo compositions. The anionic detersive surfactants are exemplified by alkali metal sulforicinates, sulfonated glyceryl esters of fatty acids, such as sulfonated monoglycerides of coconut oil acids, salts of sulfonated monovalent alcohol esters, such as sodium oleylisethianate, amides of amino sulfonic acids, such as the sodium salt of oleyl methyl tauride, sulfonated products of fatty acids nitriles, such as palmitonitrile sulfonate, sulfonated aromatic hydrocarbons, such as sodium alpha-naphthalene monosulfonate, condensation products of naphthalene sulfonic acids with formaldehyde, sodium octahydroanthracene sulfonate, alkali metal alkyl sulfates, such as sodium lauryl sulfate, ammonium lauryl sulfate or triethanol amine lauryl sulfate, ether sulfates having alkyl groups of 8 or more carbon atoms, such as sodium lauryl ether sulfate, ammonium lauryl ether sulfate, sodium alkyl aryl ether sulfates, and ammonium alkyl aryl ether sulfates, alkylarylsulfonates having 1 or more alkyl groups of 8 or more carbon atoms, alkylbenzenesulfonic acid alkali metal salts exemplified by hexylbenzenesulfonic acid sodium salt, octylbenzenesulfonic acid sodium salt, decylbenzenesulfonic acid sodium salt, dodecylbenzenesulfonic acid sodium salt, cetylbenzenesulfonic acid sodium salt, and myristylbenzenesulfonic acid sodium salt, sulfuric esters of polyoxyethylene alkyl ether including $CH_3(CH_2)_6 CH_2O(C_2H_4O)_2SO_3H$, $CH_3(CH_2)_7CH_2O(C_2H_4O)_{3.5}SO_3H$, $CH_3(CH_2)_8CH_2O(C_2H_4O)_8SO_3H$, $CH_3(CH_2)_{19}CH_2O (C_2H_4O)_4SO_3H$, and $CH_3(CH_2)_{10}CH_2O(C_2H_4O)_6SO_3H$, sodium salts, potassium salts, and amine salts of alkylnaphthylsulfonic acid. Typically, the detersive surfactant is chosen from sodium lauryl sulfate, ammonium lauryl sulfate, triethanolamine lauryl sulfate, sodium lauryl ether sulfate, and ammonium lauryl ether sulfate. The anionic detersive surfactant can be present in the shampoo composition in an amount of from about 5-50, or 5-25, wt. % based on the total weight of the shampoo composition.

The personal care composition, film, aminosiloxane polymer, and/or any other composition described above, may include at least one cationic deposition aid, typically a cationic deposition polymer. The cationic deposition aid is typically present at levels of from about 0.001-5, 0.01-1, or 0.02-0.5, % by weight. The cationic deposition polymer may be a homopolymer or be formed from two or more types of monomers. The molecular weight of the cationic deposition polymer is typically from about 5,000-10,000,000, ≥10,000, or 100,000-2,000,000. The cationic deposition polymers typically have cationic nitrogen containing groups, such as quaternary ammonium or protonated amino groups, or a combination thereof. The cationic charge density has been found to need to be at least 0.1 meq/g, typically >0.8 or higher. The cationic charge density should not exceed 4 meq/g, it is typically <3 and more typically <2 meq/g. The charge density can be measured using the Kjeldahl method and is within the above limits at the desired pH of use, which will in general be from about 3-9 or 4-8. It is contemplated that any and all values or ranges of values between those described above may also be utilized. The cationic nitrogen-containing group is typically present as a substituent on a fraction of the total monomer units of the cationic deposition polymer. Thus when the cationic deposition polymer is not a homopolymer it can include spacer noncationic monomer units. Such cationic deposition polymers are described in the CTFA Cosmetic Ingredient Directory, 3rd edition, which is expressly incorporated herein by reference in one or more non-limiting embodiments. Suitable cationic deposition aids include, for example, copolymers of vinyl monomers having cationic amine or quaternary ammonium functionalities with water soluble spacer monomers, such as (meth)acrylamide, alkyl and dialkyl (meth)acrylamides, alkyl (meth)acrylate, vinyl caprolactone and vinyl pyrrolidine. The alkyl and dialkyl substituted monomers typically have $C_1$-$C_7$ alkyl groups, more typically $C_1$-$C_3$ alkyl groups. Other suitable spacers include vinyl esters, vinyl alcohol, maleic anhydride, propylene glycol and ethylene glycol. The cationic amines can be primary, secondary or tertiary amines, depending upon the particular species and the pH of the composition. In general secondary and tertiary amines, especially tertiary, are typical. Amine substituted vinyl monomers and amines can be polymerized in the amine form and then converted to ammonium by quaternization. Suitable cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings, such as pyridinium, imidazolium, and quaternized pyrrolidine, e.g. alkyl vinyl imidazolium, and quaternized pyrrolidine, e.g. alkyl vinyl imidazolium, alkyl vinyl pyridinium, alkyl vinyl pyrrolidine salts. The alkyl portions of these monomers are typically lower alkyls, such as the $C_1$-$C_7$ alkyls, more typically $C_1$ and $C_2$ alkyls. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are typically $C_1$-$C_7$ hydrocarbyls, more typically $C_1$-$C_3$ alkyls. The cationic deposition aids can include combinations of monomer units derived from amine- and/or quaternary ammonium-substituted monomer and/or compatible spacer monomers. Suitable cationic deposition aids include, for example: copolymers of 1-vinyl-2-pyrrolidine and 1-vinyl-3-methylimidazolium salt (e.g. Chloride salt) (referred to in the industry by the Cosmetic, Toiletry, and Fragrance Association, "CTFA" as Polyquaternium-16), such as those commercially available from BASF Wyandotte Corp. (Parsippany, N.J., USA) under the LUVIQUAT trade name (e.g. LUVIQUAT FC 370); copolymers of 1-vinyl-2-pyrrolidine and dimethylaminoethyl methacrylate (referred to in the industry by CTFA as Polyquaternium-11), such as those commercially from Gar Corporation (Wayne, N.J., USA) under the GAFQUAT trade name (e.g. GAFQUAT 755N); cationic diallyl quaternary ammonium-containing polymer including, for example, dimethyl diallylammonium chloride homopolymer and copolymers of acrylamide and dimethyl diallylammonium chloride, referred to in the industry (CTFA) as Polyquaternium 6 and Polyquaternium 7, respectively; mineral acid salts of aminoalkyl esters of homo- and co-polymers of unsaturated carboxylic acids having from 3-5 carbon atoms, as described in U.S. Pat. No. 4,009,256; and cationic polyacrylamides as described in UK Application No. 9403156.4 (WO95/22311), each of which is expressly incorporated herein in one or more non-limiting embodiments. Other cationic deposition aids that can be used include polysaccharide polymers, such as cationic cellulose derivatives and cationic starch derivatives. Cationic polysaccharide polymer materials suitable for use in compositions of the disclosure include those of the formula: A-O(R—N+R1R2R3X—) wherein: A is an anhydroglucose residual group, such as starch or cellulose anhydroglucose residual, R is an alkylene oxyalkene, polyoxyalkylene, or hydroxyalkylene group, or combination thereof, R1, R2 and R3 independently are alkyl, aryl, alkylaryl, arylalkyl, alkoxyalkyl, or alkoxyaryl groups, each group containing up to 18 carbon atoms, and the total number of carbon atoms for each cationic moiety (i.e., the sum of carbon atoms in R1, R2, R3) typically being 20 or less, and X is an anionic counterion. Cationic cellulose is available from Amerchol Corp. (Edison, N.J., USA) in their Polymer iR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the trade name Polymer LM-200. Other cationic deposition aids that can be used include cationic guar gum derivatives, such as guar hydroxypropyltrimonium chloride (Commercially available from Celanese Corp. in their Jaguar trademark series). Other materials include quaternary nitrogen-containing cellulose ethers (e.g. as described in U.S. Pat. No. 3,962,418), and copolymers of etherified cellulose and starch (e.g. as described in U.S. Pat. No. 3,958,581), each of which is expressly incorporated herein by reference in one or more non-limiting embodiments.

The personal care composition, film, aminosiloxane polymer, and/or any other composition described above, may include a foam boosting agent. A foam boosting agent is an agent which increases the amount of foam available from a system at a constant molar concentration of surfactant, in contrast to a foam stabilizer which delays the collapse of a foam. Foam building is provided by adding to the aqueous media, a foam boosting effective amount of a foam boosting agent. The foam boosting agent is typically chosen from fatty acid alkanolamides and amine oxides. The fatty acid alkanolamides are exemplified by isostearic acid diethanolamide, lauric acid diethanolamide, capric acid diethanolamide, coconut fatty acid diethanolamide, linoleic acid diethanolamide, myristic acid diethanolamide, oleic acid diethanolamide, stearic acid diethanolamide, coconut fatty acid monoethanolamide, oleic acid monoisopropanolamide, and lauric acid monoisopropanolamide. The amine oxides are exemplified by N-cocodimethylamine oxide, N-lauryl dimethylamine oxide, N-myristyl dimethylamine oxide, N-stearyl dimethylamine oxide, N-cocamidopropyl dimethylamine oxide, N-tallowamidopropyl dimethylamine oxide, bis(2-hydroxyethyl) $C_{12}$-$C_{15}$ alkoxypropylamine oxide. Typically a foam boosting agent is chosen from lauric acid diethanolamide, N-lauryl dimethylamine oxide, coconut acid diethanolamide, myristic acid diethanolamide, and oleic acid diethanolamide. The foam boosting agent is typically present in the shampoo compositions in an amount from about 1-15, or 2-10, wt. % based on the total weight of the composition. The composition may further include a polyalkylene glycol to improve lather performance. Concentration of the polyalkylene glycol in the shampoo composition may be from about 0.01-5, 0.05-3, or 0.1-2, % by weight of the shampoo composition. The optional polyalkylene glycols are characterized by the general formula: $H(OCH_2CHR)_n$—OH wherein R is chosen from H, methyl, and combinations thereof. When R is H, these materials are polymers of ethylene oxide, which are also known as polyethylene oxides, polyoxyethylenes, and polyethylene glycols. When R is methyl, these materials are polymers of propylene oxide, which are also known as polypropylene oxides, polyoxypropylenes, and polypropylene glycols.

When R is methyl, it is also understood that various positional isomers of the resulting polymers can exist. In the above structure, "n" has an average value of from 1,500-25,000, 2,500-20,000, or 3,500-15,000. Polyethylene glycol polymers useful herein are PEG-2M wherein R equals H and "n" has an average value of 2,000 (PEG-2M is also known as Polyox WSR9N-10, which is available from Union Carbide and as PEG-2,000); PEG-5M wherein R equals H and "n" has an average value of 5,000 (PEG-5M is also known as Polyox WSRO N-35 and Polyox WSRS N-80, both available from Union Carbide and as PEG-5,000 and Polyethylene Glycol 300,000); PEG-7M wherein R equals H and "n" has an average value of 7,000 (PEG-7M is also known as Polyox WSRO N-750 available from Union Carbide); PEG-9M wherein R equals H and "n" has an average value of 9,000 (PEG 9-M is also known as Polyox WSRS N-3333 available from Union Carbide); and PEG-14 M wherein R equals H and "n" has an average value of 14,000 (PEG-14M is also known as Polyox WSRO N-3000 available from Union Carbide). Other useful polymers include the polypropylene glycols and mixed polyethylene/polypropylene glycols.

The personal care composition, film, aminosiloxane polymer, and/or any other composition described above, include a suspending agent at concentrations effective for suspending a silicone conditioning agent, or other water-insoluble material, in dispersed form in the personal care composition. Such concentrations may be from about 0.1-10, or 0.3-5.0, % by weight of the personal care composition. Suspending agents include crystalline suspending agents which can be categorized as acyl derivatives, long chain amine oxides, and combinations thereof, concentrations of which can be from about 0.1-5.0, or 0.5-3.0, % by weight of the shampoo compositions. These suspending agents are described in U.S. Pat. No. 4,741,855, which is expressly incorporated herein by reference in one or more non-limiting embodiments. These typical suspending agents include ethylene glycol esters of fatty acids typically having from 16-22 carbon atoms. More typical are the ethylene glycol stearates, both mono and distearate, but particularly the distearate containing <7% of the mono stearate. Other suitable suspending agents include alkanol amides of fatty acids, typically having from 16-22 carbon atoms, more typically 16-18 carbon atoms, typical examples of which include stearic monoethanolamide, stearic diethanolamide, stearic monoisopropanolamide and stearic monoethanolamide stearate. Other long chain acyl derivatives include long chain esters of long chain fatty acids (e.g. stearyl stearate, cetyl palmitate, etc.); glyceryl esters (e.g. glyceryl distearate) and long chain esters of long chain alkanol amides (e.g. stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the typical materials listed above may be used as suspending agents. For example, it is contemplated that suspending agents with long chain hydrocarbyls having $C_8$-$C_{22}$ chains may be used. Other long chain acyl derivatives suitable for use as suspending agents include N,N-dihydrocarbyl amido benzoic acid and soluble salts thereof (e.g. Na, K), particularly N,N-di(hydrogenated) C16, C18 and tallow amido benzoic acid species of this family, which are commercially available from Stepan Company (Northfield, Ill., USA). Examples of suitable long chain amine oxides for use as suspending agents include alkyl (C16-C22) dimethyl amine oxides, e.g. stearyl dimethyl amine oxide. Other suitable suspending agents include xanthan gum at concentrations ranging from about 0.3-3, or 0.4-1.2, % by weight of the shampoo compositions. The use of xanthan gum as a suspending agent is described, for example, in U.S. Pat. No. 4,788,006, which is expressly incorporated herein by reference in one or more non-limiting embodiments. Combinations of long chain acyl derivatives and xanthan gum may also be used as a suspending agent in the shampoo compositions. Such combinations are described in U.S. Pat. No. 4,704,272, which is expressly incorporated herein by reference in one or more non-limiting embodiments. Other suitable suspending agents include carboxyvinyl polymers. Typical among these polymers are the copolymers of acrylic acid cross-linked with polyallylsucrose as described in U.S. Pat. No. 2,798,053, which is expressly incorporated herein by reference in one or more non-limiting embodiments. Examples of these polymers include Carbopol 934, 940, 941, and 956, available from B.F. Goodrich Company. Other suitable suspending agents include primary amines having a fatty alkyl moiety having ≥16 carbon atoms, examples of which include palmitamine or stearamine, and secondary amines having two fatty alkyl moieties each having ≥12 carbon atoms, examples of which include dipalmitoylamine or di(hydrogenated tallow)amine. Still other suitable suspending agents include di(hydrogenated tallow)phthalic acid amide, and cross-linked maleic anhydride-methyl vinyl ether copolymer. Other suitable suspending agents may be used in the shampoo compositions, including those that can impart a gel-like viscosity to the composition, such as water soluble or colloidally water soluble polymers like cellulose ethers (e.g. methylcellulose, hydroxybutyl methylcellulose, hyroxypropylcellulose, hydroxypropyl methylcellulose, hydroxyethyl ethylcellulose and hydroxyethylcellulose), guar gum, polyvinyl alcohol, polyvinyl pyrrolidone, hydroxypropyl guar gum, starch and starch derivatives, and other thickeners, viscosity modifiers, gelling agents, etc.

The personal care composition, film, aminosiloxane polymer, and/or any other composition described above, may include one or more water-soluble emollients including, but not limited to, lower molecular weight aliphatic diols, such as propylene glycol and butylene glycol; polyols, such as glycerine and sorbitol; and polyoxyethylene polymers, such as polyethylene glycol 200. The specific type and amount of water soluble emollient(s) employed will vary depending on the desired aesthetic characteristics of the composition, and is readily determined by one skilled in the art.

The personal care composition, film, aminosiloxane polymer, and/or any other composition described above, may include one or more oils independent from the carrier fluid described above. The term "oil" as used herein describes any material which is substantially insoluble in water. Suitable oils include, but are not limited to, natural oils, such as coconut oil; hydrocarbons, such as mineral oil and hydrogenated polyisobutene; fatty alcohols, such as octyldodecanol; esters, such as $C_{12}$-$C_{15}$ alkyl benzoate; diesters, such as propylene dipelarganate; and triesters, such as glyceryl trioctanoate and silicones especially cyclomethicone and dimethicone and combinations thereof. Suitable low viscosity oils have a viscosity of about 5-100 mPas at 25° C., and are generally esters having the structure RCO—OR' wherein RCO represents the carboxylic acid radical and wherein OR' is an alcohol residue. Examples of these low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isodoecanol, polyglyceryl-3-diisostearate, or combinations thereof. The high viscosity surface oils generally have a viscosity of about 200-1,000,000, or 100,000-250,000, mPas. Surface oils include castor oil, lanolin and lanolin derivatives, triisocetyl citrate, sorbitan sesquioleate, $C_{10}$-$C_{18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof. The suggested ratio of low viscosity to high viscosity oils in the oil phase is about 1:15-15:1, or 1:10-10:1, respectively. The typical formulation of the disclosure includes about 1-20% of a combination of low viscosity and high viscosity surface oils.

Mineral oils, such as liquid paraffin or liquid petroleum, or animal oils, such as perhydrosqualene or arara oil, or alternatively of vegetable oils, such as sweet almond, calophyllum, palm, castor, avocado, jojoba, olive or cereal germ oil, may be utilized. It is also possible to use esters of lanolic acid, of oleic acid, of lauric acid, of stearic acid or of myristic acid, for example; alcohols, such as oleyl alcohol, linoleyl or linolenyl alcohol, isostearyl alcohol or octyldodecanol; or acetylglycerides, octanoates, decanoates or ricinoleates of alcohols or of polyalcohols. It is alternatively possible to use hydrogenated oils which are solid at 25° C., such as hydrogenated castor, palm or coconut oils, or hydrogenated tallow; mono-, di-, tri- or sucroglycerides; lanolins; or fatty esters which are solid at 25° C.

The personal care composition, film, aminosiloxane polymer, and/or any other composition described above, may include various waxes. The waxes generally have a melting point of from 35-120° C. at atmospheric pressure. Waxes in this category include synthetic wax, ceresin, paraffin, ozokerite, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, or combinations thereof. In one embodiment, the personal care composition includes about 10-30% of a combination of waxes. Mention may be made, among the waxes capable of being used as non-silicone fatty substances, of animal waxes, such as beeswax; vegetable waxes, such as carnauba, candelilla, ouricury or japan wax or cork fibre or sugarcane waxes; mineral waxes, for example paraffin or lignite wax or microcrystalline waxes or ozokerites; synthetic waxes, including polyethylene waxes, and waxes obtained by the Fischer-Tropsch synthesis. Mention may be made, among the silicone waxes, of polymethylsiloxane alkyls, alkoxys and/or esters.

The personal care composition, film, aminosiloxane polymer, and/or any other composition described above, may include a powder. The powder can be generally defined as dry, particulate matter having a particle size of about 0.02-50 microns. The powder may be colored or non-colored (for example white). Suitable powders include bismuth oxychloride, titanated mica, fumed silica, spherical silica beads, polymethylmethacrylate beads, micronized teflon, boron nitride, acrylate polymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium carbonate, magnesium hydroxide, magnesium oxide, magnesium silicate, magnesium trisilicate, maltodextrin, montmorillonite, microcrystalline cellulose, rice starch, silica, talc, mica, titanium dioxide, zinc laurate, zinc myristate, zinc neodecanoate, zinc rosinate, zinc stearate, polyethylene, alumina, attapulgite, calcium carbonate, calcium silicate, dextran, kaolin, nylon, silica silylate, silk powder, serecite, soy flour, tin oxide, titanium hydroxide, trimagnesium phosphate, walnut shell powder, or combinations thereof. The powder may be surface treated with lecithin, amino acids, mineral oil, silicone oil, or various other agents either alone or in combination, which coat the powder surface and render the particles hydrophobic in nature.

The powder can also include or be an organic and/or inorganic pigment. Organic pigments are generally various aromatic types including azo, indigoid, triphenylmethane, anthraquinone, and xanthine dyes which are designated as D&C and FD&C blues, browns, greens, oranges, reds, yellows, etc. Inorganic pigments generally consist of insoluble metallic salts of certified color additives, referred to as the Lakes or iron oxides. A pulverulent coloring agent, such as carbon black, chromium or iron oxides, ultramarines, manganese pyrophosphate, iron blue, and titanium dioxide, pearlescent agents, generally used as a combination with colored pigments, or some organic dyes, generally used as a combination with colored pigments and commonly used in the cosmetics industry, can be added to the composition. In general, these coloring agents can be present in an amount by weight from 0-20% with respect to the weight of the personal care composition, film, aminosiloxane polymer, and/or any other composition described above.

Pulverulent inorganic or organic fillers can also be added, generally in an amount by weight from about 0-40% with respect to the weight of the personal care composition, film, aminosiloxane polymer, and/or any other composition described above. These pulverulent fillers can be chosen from talc, micas, kaolin, zinc or titanium oxides, calcium or magnesium carbonates, silica, spherical titanium dioxide, glass or ceramic beads, metal soaps derived from carboxylic acids having 8-22 carbon atoms, non-expanded synthetic polymer powders, expanded powders and powders from natural organic compounds, such as cereal starches, which may or may not be cross-linked. The fillers may typically be present in a proportion of from about 0-35, or 5-15, % of the total weight of the composition. Mention may be made in particular of talc, mica, silica, kaolin, nylon powders (in particular ORGASOL), polyethylene powders, Teflon, starch, boron nitride, copolymer microspheres, such as EXPANCEL (Nobel Industrie), polytrap and silicone resin microbeads (TOSPEARL from Toshiba, for example).

The personal care composition, film, aminosiloxane polymer, and/or any other composition described above, may include a sunscreen. Sunscreens typically absorb ultraviolet light between 290-320 nanometers (the UV-B region) such as, but not exclusively, para-aminobenzoic acid derivatives and cinnamates, such as octyl methoxycinnamate and those which absorb ultraviolet light in the range of 320-400 nanometers (the UV-A region), such as benzophenones and butyl methoxy dibenzoylmethane. Some additional examples of sunscreens are 2-ethoxyethyl p-methoxycinnamate; menthyl anthranilate; homomethyl salicylate; glyceryl p-aminobenzoate; isobutyl p-aminobenzoate; isoamyl p-dimethylaminobenzoate; 2-hydroxy-4-methoxybenzophenones sulfonic acid; 2,2'-dihydroxy-4-methoxybenzophenone; 2-hydroxy-4-methoxybenzophenone; 4-mono and 4-bis(3-hydroxy-propyl)amino isomers of ethyl benzoate;

and 2-ethylhexyl p-dimethylaminobenzoate. In various embodiments, the sunscreen is as described in EP-A-678, 292, which is expressly incorporated herein by reference in one or more non-limiting embodiments. In various embodiments, sunscreens include at least one carboxylic or better still sulphonic acid radical. This acid radical can be in free form or in partially or totally neutralized form. It is possible to use one or more hydrophilic screening agents containing acid functionality. As examples of acidic screening agents containing at least one $SO_3H$ group, mention may be made more particularly of 3-benzylidine-2-camphorsulphonic derivatives. A particularly typical compound is benzene-1, 4-[di(3-methylidenecamphor-10-sulphonic acid)]. This screening agent is a broad-band screening agent capable of absorbing ultraviolet rays with wavelengths of between 280 nm and 400 nm, with absorption maxima of between 320 nm and 400 nm, in particular at 345 nm. It is used in acid form or salified with a base chosen from triethanolamine, sodium hydroxide and potassium hydroxide. In addition, it can be in cis or trans form. This screening agent is known under the trade name Mexoryl SX. Other specific examples are 4-(3-methylidenecamphor)benzenesulphonic acid, 3-benzylidenecamphor-10-sulphonic acid, 2-methyl-5-(3-methylidenecamphor)benzenesulphonic acid, 2-chloro-5-(3-methylidenecamphor)benzenesulphonic acid, 3-(4-methyl)benzylidenecamphor-10-sulphonic acid, (3-t-butyl-2-hydroxy-5-methyl)benzylidenecamphor-10-sulphonic acid, (3-t-butyl-2-hydroxy-5-methoxy)benzylidenecamphor-10-sulphonic acid, (3,5-di-tert-butyl-4-hydroxy)benzylidenecamphor-10-sulphonic acid, 2-methoxy-5-(3-methylidenecamphor)benzenesulphonic acid, 3-(4,5-methylenedioxy)benzylidenecamphor-10-sulphonic acid, 3-(4-methoxy)benzylidenecamphor-10-sulphonic acid, 3-(4,5-dimethoxy)benzylidenecamphor-10-sulphonic acid, 3-(4-n-butoxy)benzylidenecamphor-10-sulphonic acid, 3-(4-n-butoxy-5-methoxy)benzylidenecamphor-10-sulphonic acid, 2-[4-(camphormethylidene)phenyl]benzimidazole-5-sulphonic acid. Suitable compounds are described in U.S. Pat. No. 4,585,597, and FR 2,236,515, 2,282,426, 2,645,148, 2,430, 938 and 2,592,380, each of which is expressly incorporated herein by reference in one or more non-limiting embodiments. The screening agent containing a sulphonic group can also be a sulphonic derivative of benzophenone or 2-phenylbenzimidazole-5-sulphonic acid, having excellent photoprotective power in the UV-B radiation range and is sold under the trade name "Eusolex 232" by Merck, benzene-1,4-di(benzimidazol-2-yl-5-sulphonic acid), benzene-1,4-di(benzoxazol-2-yl-5-sulphonic acid). The hydrophilic screening agent(s) can be present in the final composition according to the disclosure in a content which can be from about 0.1-20%, or 0.2-10%, by weight relative to the total weight of the personal care composition.

Additional lipophilic screening agents can be utilized, such as those derived from dibenzoylmethane and more especially 4-tert-butyl-4'-methoxydibenzoylmethane, which effectively have a high intrinsic power of absorption. These dibenzoylmethane derivatives, which are products that are well known per se as UV-A active screening agents, are described in particular in French patent applications FR-A-2,326,405 and FR-A-2,440,933, as well as in European patent application EP-A-0,114,607, each of which is expressly incorporated herein by reference in one or more non-limiting embodiments. 4-(tert-butyl)-4'-methoxydibenzoylmethane is currently sold under the trade name "Parsol 1789" by Givaudan. Another dibenzoylmethane derivative which is typical according to the present disclosure is 4-isopropyldibenzoylmethane, this screening agent being sold under the name "Eusolex 8020" by Merck. Similarly octocrylene, a liquid lipophilic screening agent that is already known for its activity in the UV-B range is commercially available, and is sold in particular under the name "Uvinul N 539" by BASF. As another lipophilic (or liposoluble) screening agent which can be used in the disclosure, mention may also be made of p-methylbenzylidenecamphor, which is also known as a UV-B absorber and is sold in particular under the trade name "Eusolex 6300" by Merck. The lipophilic screening agent(s) can be present in the composition according to the disclosure in a content which can be from about 0.5-30%, or 0.5-20%, of the total weight of the personal care composition, film, aminosiloxane polymer, and/or any other composition described above. Other examples of lipophilic or hydrophilic organic screening agents are described in patent application EP-A-0,487,404, which is expressly incorporated herein by reference in one or more non-limiting embodiments. The cosmetic and/or dermatological compositions according to the disclosure can also include pigments or alternatively nano-pigments (average primary particle size: generally between 5 nm and 100 nm, typically between 10 and 50 nm) of coated or uncoated metal oxides, such as, for example, nano-pigments of titanium oxide (amorphous or crystallized in rutile and/or anatase form), of iron oxide, of zinc oxide, of zirconium oxide or of cerium oxide, which are all photoprotective agents that are well known per se and which act by physically blocking (reflection and/or scattering) UV radiation. Standard coating agents are, moreover, alumina and/or aluminum stearate, and silicones. Such coated or uncoated metal oxide nano-pigments are described in particular in patent applications EP-A-0,518,772 and EP-A-0,518,773, each of which is expressly incorporated herein by reference in one or more non-limiting embodiments.

A thickening agent may be utilized to provide a convenient viscosity for any composition described above. For example, viscosities of from about 500-25,000, or 3,000-7, 000, $mm^2/s$ at 25° C. may be obtained. Suitable thickening agents are exemplified by sodium alginate, gum arabic, polyoxyethylene, guar gum, hydroxypropyl guar gum, ethoxylated alcohols, such as laureth-4 or polyethylene glycol 400, cellulose derivatives exemplified by methylcellulose, methylhydroxypropylcellulose, hydroxypropylcellulose, polypropylhydroxyethylcellulose, starch, and starch derivatives exemplified by hydroxyethylamylose and starch amylose, locust bean gum, electrolytes exemplified by sodium chloride and ammonium chloride, and saccharides, such as fructose and glucose, and derivatives of saccharides, such as PEG-120 methyl glucose diolate or combinations of 2 or more of these. Alternatively, the thickening agent is chosen from cellulose derivatives, saccharide derivatives, and electrolytes, or from a combination of two or more of the above thickening agents exemplified by a combination of a cellulose derivative and any electrolyte, and a starch derivative and any electrolyte. The thickening agent, where used is present in a shampoo composition, may provide a viscosity of from about 500-25,000 $mm^2/s$ at 25° C. Alternatively, the thickening agent may be present in an amount from about 0.05-10, or 0.05-5, wt % based on the total weight of the personal care composition, film, aminosiloxane polymer, and/or any other composition described above.

Stabilizing agents can also be used. Suitable water phase stabilizing agents can include alone or in combination one or more electrolytes, polyols, alcohols, such as ethyl alcohol, and hydrocolloids. Typical electrolytes are alkali metal salts and alkaline earth salts, especially the chloride, borate, citrate, and sulfate salts of sodium, potassium, calcium and magnesium, as well as aluminum chlorohydrate, and polyelectrolytes, especially hyaluronic acid and sodium hyaluronate. When the stabilizing agent is, or includes, an electrolyte, it amounts to about 0.1-5, or 0.5-3, wt % of the personal care composition, film, aminosiloxane polymer, and/or any other composition described above. The hydrocolloids include gums, such as Xantham gum or Veegum and thickening agents, such as carboxymethyl cellulose. Polyols, such as glycerine, glycols, and sorbitols can also be used. Alternative polyols are glycerine, propylene glycol, sorbitol, and butylene glycol. If a large amount of a polyol is used, one need not add the electrolyte. However, it is typical to use a combination of an electrolyte, a polyol and a hydrocolloid to stabilize the water phase, e.g. magnesium sulfate, butylene glycol and Xantham gum.

Any of the aforementioned compositions may also be or include antiperspirant agents and deodorant agents, such as Aluminum Chloride, Aluminum Zirconium Tetrachlorohydrex GLY, Aluminum Zirconium Tetrachlorohydrex PEG, Aluminum Chlorohydrex, Aluminum Zirconium Tetrachlorohydrex PG, Aluminum Chlorohydrex PEG, Aluminum Zirconium Trichlorohydrate, Aluminum Chlorohydrex PG, Aluminum Zirconium Trichlorohydrex GLY, Hexachlorophene, Benzalkonium Chloride, Aluminum Sesquichlorohydrate, Sodium Bicarbonate, Aluminum Sesquichlorohydrex PEG, Chlorophyllin-Copper Complex, Triclosan, Aluminum Zirconium Octachlorohydrate, and Zinc Ricinoleate.

The personal care composition, film, aminosiloxane polymer, and/or any other composition described above, can be an aerosol in combination with propellant gases, such as carbon dioxide, nitrogen, nitrous oxide, volatile hydrocarbons, such as butane, isobutane, or propane and chlorinated or fluorinated hydrocarbons, such as dichlorodifluoromethane and dichlorotetrafluoroethane or dimethylether.

Silicone compositions, other than the present aminosiloxane polymer may also be included in the personal care composition, film, aminosiloxane polymer, and/or any other composition described above. For example, such silicones include silicone fluids, gums, resins, elastomers; silicone surfactants and emulsifiers, such as silicone polyethers, organofunctional silicones, such as amino functional silicones and alkylmethylsiloxanes. Alkylmethylsiloxanes may be included in the present compositions. These siloxane polymers generally typically have the formula $Me_3SiO[Me_2SiO]_y[MeRSiO]_zSiMe_3$, in which R is a hydrocarbon group containing 6-30 carbon atoms, Me represents methyl, and the Dp (i.e., the sum of "y" and "z") is 3-50. Both the volatile and liquid species of alkylmethysiloxanes can be used in the composition.

Silicone gums may also be included in the personal care composition, film, aminosiloxane polymer, and/or any other composition described above. Suitable non-limiting gums include insoluble polydiorganosiloxanes having a viscosity >1,000,000 centistoke (mm2/s) at 25° C., alternatively >5,000,000 centistoke ($mm^2/s$) at 25° C. These silicone gums are typically sold as compositions already dispersed in a suitable solvent to facilitate their handling. Ultra-high viscosity silicones can also be included as optional ingredients. These ultra-high viscosity silicones typically have a kinematic viscosity >5 million centistoke ($mm^2/s$) at 25° C. up to 20 million centistoke ($mm^2/s$) at 25° C. Compositions of this type in are described for example in U.S. Pat. No. 6,013,682, which is expressly incorporated herein by reference in one or more non-limiting embodiments.

Silicone resins may also be included in the personal care composition, film, aminosiloxane polymer, and/or any other composition described above. These resins are generally highly cross-linked polymeric siloxanes. Cross-linking is typically obtained by incorporating trifunctional and/or tetrafunctional silanes with the monofunctional silane and/or difunctional silane monomers used during manufacture. The degree of cross-linking required to obtain a suitable silicone resin will vary according to the specifics of silane monomer units incorporated during manufacture of the silicone resin. In general, any silicone having a sufficient level of trifunctional and tetrafunctional siloxane monomer units, and hence possessing sufficient levels of cross-linking to dry down to a rigid or a hard film can be used. Commercially available silicone resins suitable for applications herein are generally supplied in an unhardened form in low viscosity, volatile or nonvolatile silicone fluids. The silicone resins may be incorporated into compositions of the disclosure in their non-hardened forms rather than as hardened resinous structures.

Silicone carbinol fluids may be included in the personal care composition, film, aminosiloxane polymer, and/or any other composition described above. These materials can be commonly described as substituted hydrocarbyl functional siloxane fluids or resins and some are described in WO 03/101412 A2, which is expressly incorporated herein by reference in one or more non-limiting embodiments.

Water soluble or water dispersible silicone polyethers may also be included in the personal care composition, film, aminosiloxane polymer, and/or any other composition described above. These are also known as polyalkylene oxide silicone copolymers, silicone poly(oxyalkylene) copolymers, silicone glycol copolymers, or silicone surfactants. These can be linear rake or graft type materials, or ABA type where the B is the siloxane polymer block, and the A is the poly(oxyalkylene) group. The poly(oxyalkylene) group can consist of polyethylene oxide, polypropylene oxide, or mixed polyethylene oxide/polypropylene oxide groups. Other oxides, such as butylene oxide or phenylene oxide are also possible.

Any of the personal care composition, film, aminosiloxane polymer, and/or any other composition described above may also include a solvent, such as (i) organic compounds, (ii) compounds containing a silicon atom, (iii) mixtures of organic compounds, (iv) mixtures of compounds containing a silicon atom, or (v) mixtures of organic compounds and compounds containing a silicon atom; used on an industrial scale to dissolve, suspend, or change the physical properties of other materials.

In general, the organic compounds are aromatic hydrocarbons, aliphatic hydrocarbons, alcohols, aldehydes, ketones, amines, esters, ethers, glycols, glycol ethers, alkyl halides, or aromatic halides. Representative of some common organic solvents are alcohols, such as methanol, ethanol, 1-propanol, cyclohexanol, benzyl alcohol, 2-octanol, ethylene glycol, propylene glycol, and glycerol; aliphatic hydrocarbons, such as pentane, cyclohexane, heptane, VM&P solvent, and mineral spirits; alkyl halides, such as chloroform, carbon tetrachloride, perchloroethylene, ethyl chloride, and chlorobenzene; amines, such as isopropylamine, cyclohexylamine, ethanolamine, and diethanolamine; aromatic hydrocarbons, such as benzene, toluene, ethylbenzene, and xylene; esters, such as ethyl acetate, isopropyl acetate, ethyl acetoacetate, amyl acetate, isobutyl isobutyrate, and benzyl acetate; ethers, such as ethyl ether, n-butyl ether, tetrahydrofuran, and 1,4-dioxane; glycol ethers, such as ethylene glycol monomethyl ether, ethylene glycol monomethyl ether acetate, diethylene glycol monobutyl ether, and propylene glycol monophenyl ether; ketones, such as acetone, methyl ethyl ketone, cyclohexanone, diacetone alcohol, methyl amyl ketone, and diisobutyl ketone; petroleum hydrocarbons, such as mineral oil, gasoline, naphtha, kerosene, gas oil, heavy oil, and crude oil; lubricating oils, such as spindle oil and turbine oil; and fatty oils, such as corn oil, soybean oil, olive oil, rapeseed oil, cotton seed oil, sardine oil, herring oil, and whale oil.

"Other" miscellaneous organic solvents can also be used, such as acetonitrile, nitromethane, dimethylformamide, propylene oxide, trioctyl phosphate, butyrolactone, furfural, pine oil, turpentine, and m-creosol.

Solvents may also include volatile flavoring agents, such as oil of wintergreen; peppermint oil; spearmint oil; menthol; vanilla; cinnamon oil; clove oil; bay oil; anise oil; *eucalyptus* oil; thyme oil; cedar leaf oil; oil of nutmeg; oil of sage; *cassia* oil; cocoa; licorice; high fructose corn syrup; citrus oils, such as lemon, orange, lime, and grapefruit; fruit essences, such as apple, pear, peach, grape, strawberry, raspberry, cherry, plum, pineapple, and apricot; and other useful flavoring agents including aldehydes and esters, such as cinnamyl acetate, cinnamaldehyde, eugenyl formate, p-methylanisole, acetaldehyde, benzaldehyde, anisic aldehyde, citral, neral, decanal, vanillin, tolyl aldehyde, 2,6-dimethyloctanal, and 2-ethyl butyraldehyde.

Moreover, solvents may include volatile fragrances, such as natural products and perfume oils. Some representative natural products and perfume oils are ambergris, benzoin, civet, clove, leaf oil, jasmine, mate, *mimosa*, musk, myrrh, orris, sandalwood oil, and vetivert oil; aroma chemicals, such as amyl salicylate, amyl cinnamic aldehyde, benzyl acetate, citronellol, coumarin, geraniol, isobornyl acetate, ambrette, and terpinyl acetate; and the various classic family perfume oils, such as the floral bouquet family, the oriental family, the chypre family, the woody family, the citrus family, the canoe family, the leather family, the spice family, and the herbal family.

EXAMPLES

Other components that may be used for purposes of this disclosure are described in PCT/US15/024905 and PCT/US15/024886, each of which is expressly incorporated herein by reference in one or more non-limiting embodiments. The following examples are intended to illustrate and not to limit the invention.

Example 1A: Formation of Cross-Linked Aminosiloxane Polymer at 0.33 Mol Ratio

To an 8 oz. reaction vessel the following components were charged: 2.57 g of a 5 Dp pendant aminopropyl siloxane and 0.44 g of maleic anhydride along with 3.00 g of d-chloroform. This reaction mixture was heated in a 55° C. water bath for 5 hours producing a viscous, slightly yellow liquid. In the proton NMR spectrum set forth in the bottom of FIG. 1, there is a lack of $sp^3$ protons, which would have resulted from the Michael addition of the aminosiloxane at 4.52 ppm, and the presence of $sp^2$ protons at 6.91 ppm.

Example 1B: Formation of Cross-Linked Aminosiloxane Polymer at 0.21 Mol Ratio

To an 8 oz. reaction vessel the following components were charged: 1.79 g of a 5 Dp pendant aminopropyl siloxane and 0.21 g of maleic anhydride. This reaction mixture was heated to a higher reaction temperature of 70° C. for 2.5 hours. The reaction product is a viscous, slightly yellow liquid. In the proton NMR spectrum set forth in the top of FIG. 1, there is an appearance of the sp3 proton resulting from the Michael addition of the aminosiloxane at 4.52 ppm, and the partial consumption of $sp^2$ protons (from the same carbon) at 6.91 ppm.

Example 2: Formation of Cross-Linked Aminosiloxane Polymer at 0.25 Mol Ratio

Figure 2:
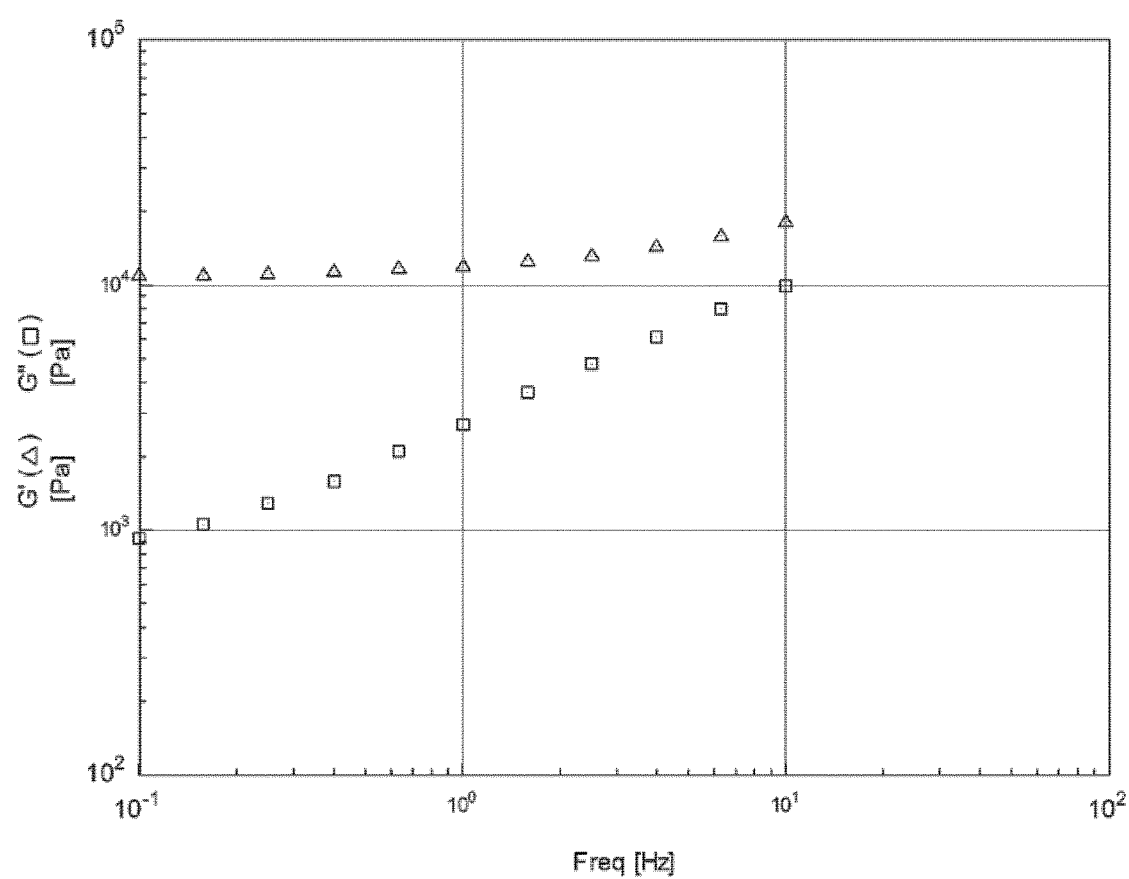
FIG. 2 is a plot of frequency modulation as related to Example 2.
Figure 3:
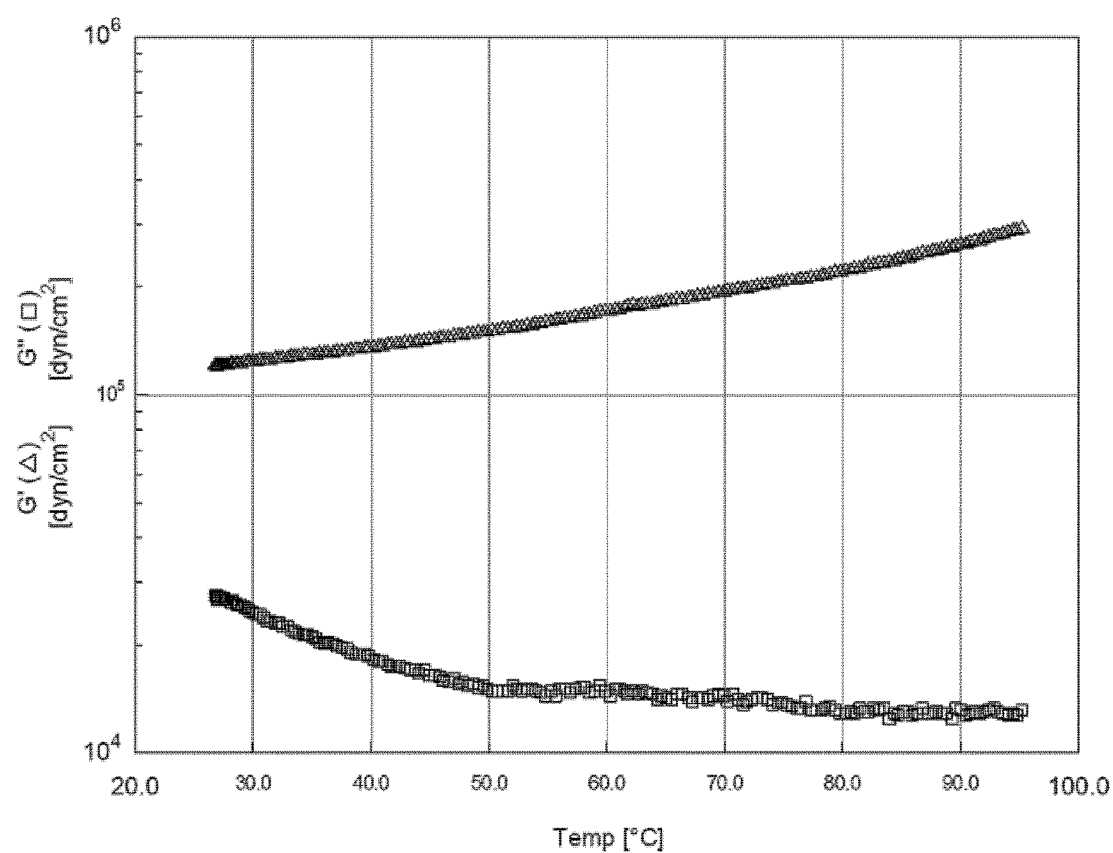
FIG. 3 is a plot of temperature modulation as also related to Example 2.

To an 8 oz. reaction vessel the following components were charged: 49.09 g of a pendant aminopropyl siloxane of the structure $(MD_{94}D^A{}_6M$; where "A" is an aminopropyl group) and 0.91 g of maleic anhydride. This reaction mixture was heated in an isothermal oven at 70° C. for 2.5 hours. The reaction product is a firm, extensively cross-linked gel that is optically clear with no detectable amine odor. Results of frequency modulation experiments (depicted in FIG. 2) provide evidence for cross-linking through comparison of the storage modulus (G') and loss modulus (G") where the G' is higher than G" for a cross-linked aminosiloxane polymer. Results of temperature sweep experiments (depicted in FIG. 3) provide evidence for cross-linking through comparison of the storage modulus (G') and loss modulus (G") where the G' is higher than G" for a cross-linked aminosiloxane polymer.

Example 3: Formation of Cross-Linked Aminosiloxane Polymer at 0.33 Mol Ratio

Figure 4:
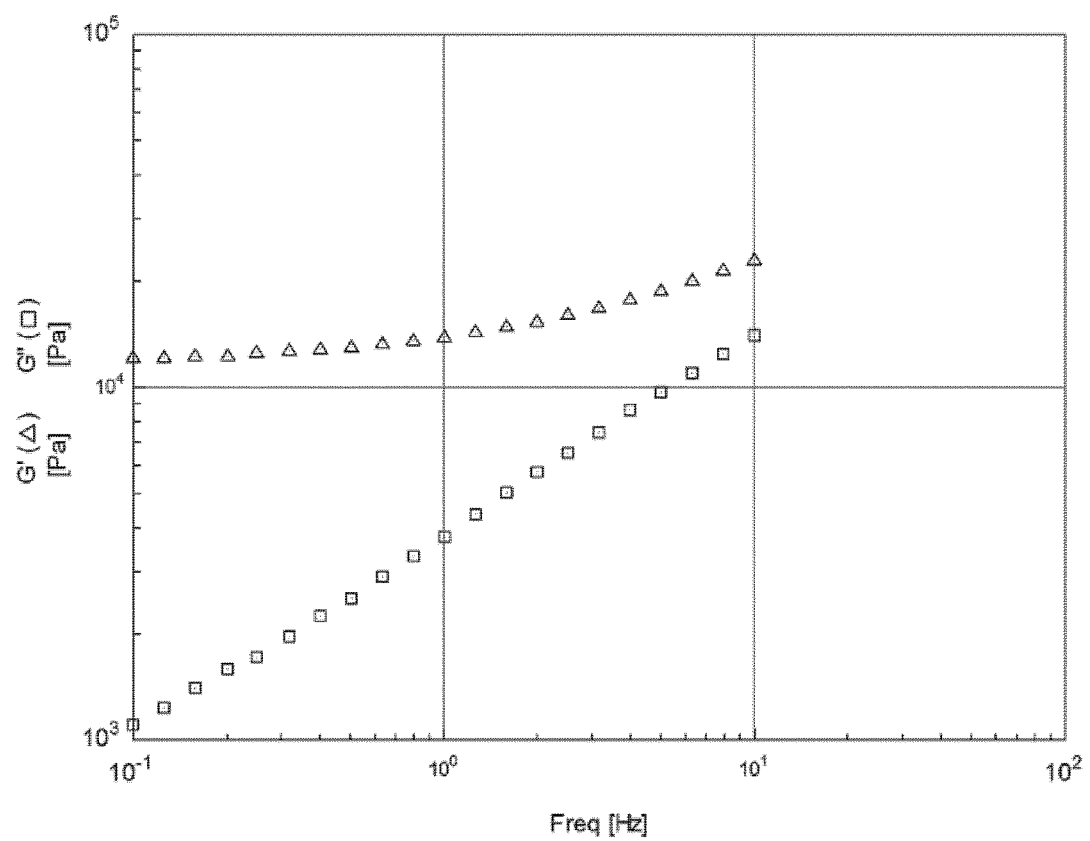
FIG. 4 is a plot of frequency modulation as related to Example 3.

To an 8 oz. reaction vessel the following components were charged: 48.80 g of a pendant aminopropyl siloxane of the structure (MD94DA6M) and 1.22 g of maleic anhydride. This reaction mixture was heated in an isothermal oven at 70° C. for 2.5 hours. The reaction product is a firm, extensively cross-linked gel that is optically clear with no detectable amine odor. Results of frequency modulation experiments (depicted in FIG. 4) provide strong evidence for cross-linking through comparison of the storage modulus (G') and loss modulus (G").

Example 4: Formation of Cross-Linked Aminosiloxane Polymer at 0.23 Mol Ratio

Figure 5:
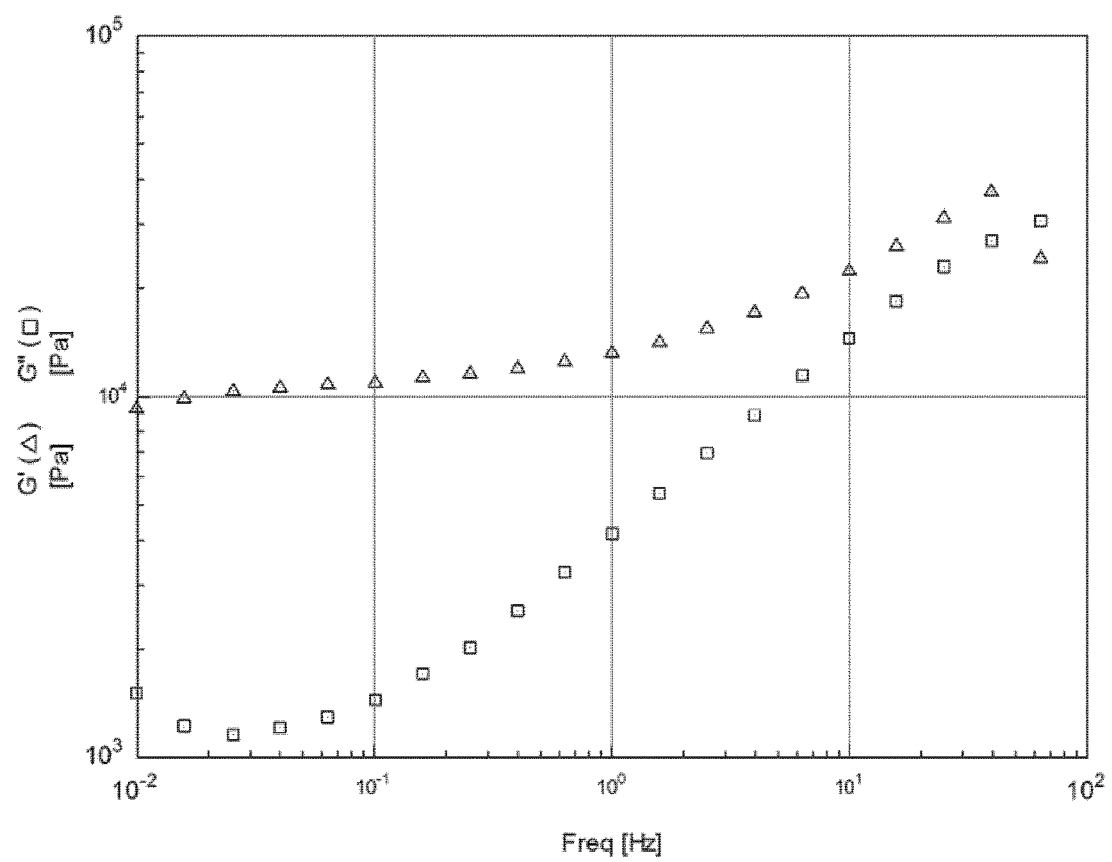
FIG. 5 is a plot of frequency modulation as related to Example 4.

To an 8 oz. reaction vessel the following components were charged: 1.26 g of itaconic anhydride and 58.74 g of a 100 Dp pendant aminopropyl siloxane. This reaction mixture was heated in an 80° C. water bath for 5 hours producing a gel. In the frequency sweep set forth in FIG. 5, the product is confirmed as cross-linked as the storage modulus (G') is greater than the loss modulus (G").

In various non-limiting embodiments, this disclosure includes one or more emulsions, compounds, reactants, method steps, or any other portion of the disclosure of PCT/US15/20640, which is expressly incorporated herein in its entirety in these non-limiting embodiments.

The terms "comprising" or "comprise" are used herein in their broadest sense to mean and encompass the notions of "including", "include", "consist(ing) essentially of", and "consist(ing) of". The use of "for example", "e.g.", "such as", and "including" to list illustrative examples does not limit to only the listed examples. Thus, "for example" or "such as" means "for example, but not limited to" or "such as, but not limited to" and encompasses other similar or equivalent examples. The term "about" as used herein serves to reasonably encompass or describe minor variations in numerical values measured by instrumental analysis or as a result of sample handling. Such minor variations may be in the order of ±0-10, ±0-5, or ±0-2.5, % of the numerical values. Further, The term "about" applies to both numerical values when associated with a range of values. Moreover, the term "about" may apply to numerical values even when not explicitly stated. Generally, as used herein a hyphen "-" or dash "—" in a range of values is "to" or "through"; a ">" is "above" or "greater-than"; a "≥" is "at least" or "greater-than or equal to"; a "<" is "below" or "less-than"; and a "≤" is "at most" or "less-than or equal to". On an individual basis, each of the aforementioned applications for patent, patents, and/or patent application publications, is expressly incorporated herein by reference in its entirety in one or more non-limiting embodiments. One or more of the values described above may vary by ±5%, ±10%, ±15%, ±20%, ±25%, etc. so long as the variance remains within the scope of the disclosure. Unexpected results may be obtained from each member of a Markush group independent from all other members. Each member may be relied upon individually and or in combination and provides adequate support for specific embodiments within the scope of the appended claims. The subject matter of all combinations of independent and dependent claims, both single and multiple dependent, is herein expressly contemplated. It is contemplated that any and all values or ranges of values between those described above may also be utilized. Moreover, all combinations of all chemistries, compounds, and concepts described above, and all values of subscripts and superscripts described above, are expressly contemplated in various non-limiting embodiments. The disclosure is illustrative including words of description rather than of limitation. Many modifications and variations of the present disclosure are possible in light of the above teachings, and the disclosure may be practiced otherwise than as specifically described herein.

What is claimed is:

1. A cross-linked aminosiloxane polymer comprising a first siloxane backbone, a second siloxane backbone, and at least one intramolecular structure cross-linking a silicon atom of said first siloxane backbone and a silicon atom of said second siloxane backbone, wherein said intramolecular structure has the chemical structure:

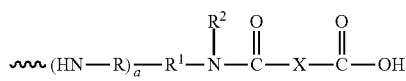

wherein X is chosen from the following groups;

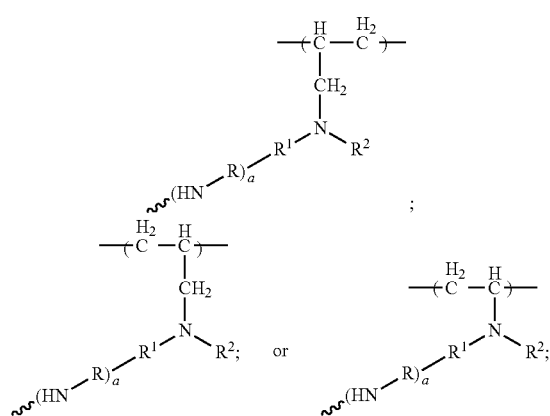

wherein each R is independently a $C_1$-$C_{10}$ hydrocarbon group; each $R^1$ is independently a $C_1$-$C_{10}$ hydrocarbon group; each $R^2$ is independently a hydrogen atom, OH, a $C_1$-$C_{12}$ hydrocarbon group, a phenyl group, R'(OR")$_m$, or R'OH, where each of R' and R" is independently an alkyl group and "m" is 1 to 3; and "a" is 0 or 1.

2. The cross-linked aminosiloxane polymer of claim 1, having the chemical structure:

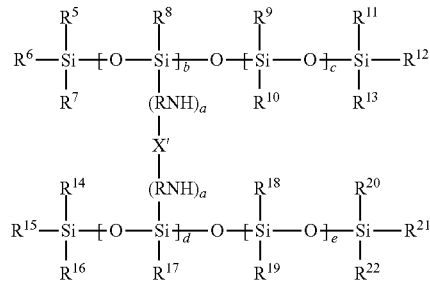

wherein X' is chosen from the following groups;

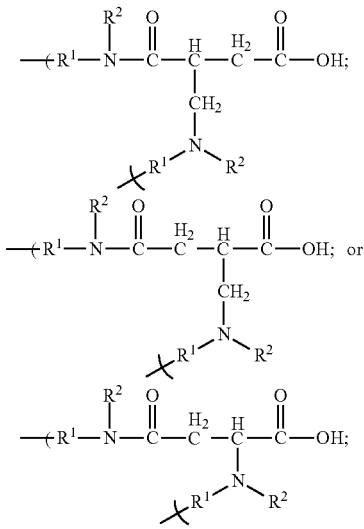

wherein each of R, $R^1$, $R^2$ and "a" is as defined above; each of $R^5$-$R^{22}$ is independently a hydrogen atom, a $C_1$-$C_{12}$ hydrocarbon group, a $C_2$-$C_{30}$ alkenyl group, a $C_6$-$C_{12}$ aromatic group, R'(OR")$_m$, or a polyalkyleneoxy group, where each of R', R", and "m" is as defined above; each of "b" and "d" is independently from 1 to 100; and each of "c" and "e" is independently from 1 to 3,000.

3. The cross-linked aminosiloxane polymer of claim 1, wherein said first siloxane backbone has the chemical structure:

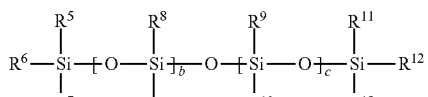

wherein each of $R^5$-$R^{13}$ is independently a hydrogen atom, a $C_1$-$C_{12}$ hydrocarbon group, a $C_2$-$C_{30}$ alkenyl group, a $C_6$-$C_{12}$ aromatic group, R'(OR")$_m$, or a polyalkyleneoxy group, where each of R' and R" is independently an alkyl group and "m" is 1 to 3; "b" is from 1 to 100; "c" is from 1 to 3,000; and "L" is said intramolecular structure.

4. The cross-linked aminosiloxane polymer of claim 1, wherein said second siloxane backbone has the chemical structure:

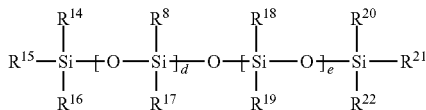

wherein each of $R^{14}$-$R^{22}$ is independently a hydrogen atom, a $C_1$-$C_{12}$ hydrocarbon group, a $C_2$-$C_{30}$ alkenyl group, a $C_6$-$C_{12}$ aromatic group, R'(OR")$_m$, or a polyalkyleneoxy group, where each of R' and R" is independently an alkyl group and "m" is 1 to 3; "d" is from 1 to 100; "e" is from 1 to 3,000; and "L" is said intramolecular structure.

5. The cross-linked aminosiloxane polymer of claim 1, comprising the reaction product of:
   a polyorganosiloxane having an amino group; and
   a polyorganosiloxane that has an α,β-unsaturated carboxy acid amide group.

6. The cross-linked aminosiloxane polymer of claim 5, wherein said polyorganosiloxane having an amino group has the chemical formula:

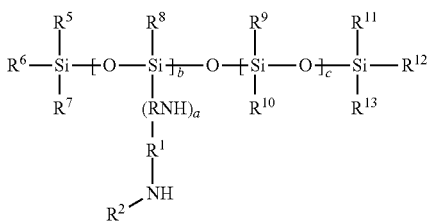

wherein each of R, $R^1$, $R^2$ and "a" is as defined above; each of $R^5$-$R^{13}$ is independently a hydrogen atom, a $C_1$-$C_{12}$ hydrocarbon group, a $C_2$-$C_{30}$ alkenyl group, a $C_6$-$C_{12}$ aromatic group, R'(OR")$_m$, or a polyalkyleneoxy group, where each of R', R", and "m" is as defined above; "b" is from 1 to 100; and "c" is from 1 to 3,000.

7. The cross-linked aminosiloxane polymer of claim 5, wherein said polyorganosiloxane that has an α,β-unsaturated carboxy acid amide group has one of the following chemical formulas:

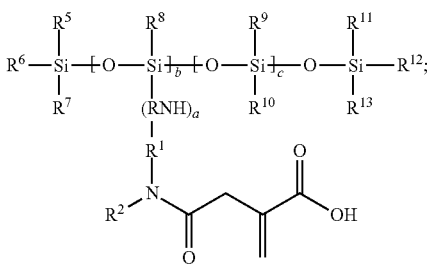

-continued

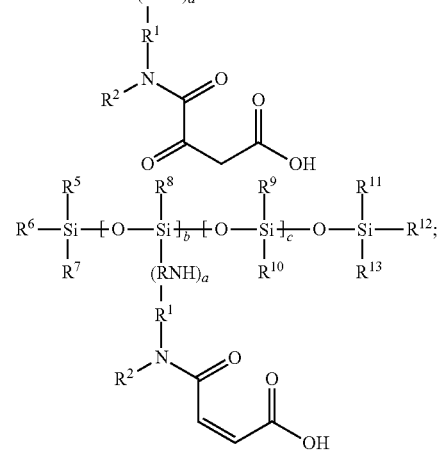

wherein each of R, $R^1$, $R^2$, "a", $R^5$-$R^{13}$, "b", and "c" is as defined above.

8. The cross-linked aminosiloxane polymer of claim 7, wherein said polyorganosiloxane that has an α,β-unsaturated carboxy acid amide group is the reaction product of:
   a second polyorganosiloxane having an amino group; and
   maleic anhydride and/or itaconic anhydride.

9. The cross-linked aminosiloxane polymer of claim 8, wherein said maleic anhydride and/or said itaconic anhydride reacts in an amount of from about 0.01 to about 0.33 moles per 1 mole of said amino group of said second organopolysiloxane.

10. The cross-linked aminosiloxane polymer of claim 1, wherein:
   i) R is independently a $C_1$-$C_6$ hydrocarbon group;
   ii) "a" is 1; or
   iii) both i) and ii).

11. A composition comprising the cross-linked aminosiloxane polymer as set forth in claim 1, said composition chosen from cosmetic compositions, fabric treating compositions, fiber treating compositions, hair care compositions, fiber care compositions, and combinations thereof.

12. A method of forming a cross-linked aminosiloxane polymer, said method comprising the steps of:
   providing a polyorganosiloxane having an amino group;
   providing maleic anhydride and/or itaconic anhydride; and
   combining the maleic anhydride and/or itaconic anhydride and the polyorganosiloxane having an amino group to form the cross-linked aminosiloxane polymer;
   wherein the cross-linked aminosiloxane polymer comprises a first siloxane backbone, a second siloxane backbone, and at least one intramolecular structure cross-linking a silicon atom of the first siloxane backbone and a silicon atom of the second siloxane backbone, wherein the intramolecular structure has the chemical structure:

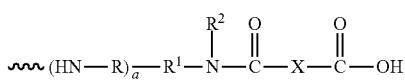

wherein X is chosen from the following groups:

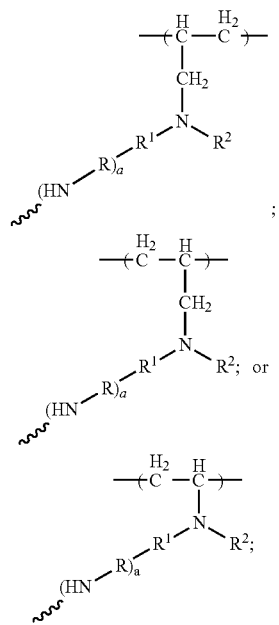

wherein each R is independently a $C_1$-$C_{10}$ hydrocarbon group; each $R^1$ is independently a $C_1$-$C_{10}$ hydrocarbon group; each $R^2$ is independently a hydrogen atom, OH, a $C_1$-$C_{12}$ hydrocarbon group, a phenyl group, R'(OR")$_m$, or R'OH, where each of R' and R" is independently an alkyl group and "m" is 1 to 3; and "a" is 0 or 1.

13. The method of claim 12, further comprising the step of heating the polyorganosiloxane having an amino group and the maleic anhydride and/or itaconic anhydride to a temperature of from about −20° C. to about 100° C.

14. The method of claim 12, wherein the step of providing the maleic anhydride and/or itaconic anhydride is further defined as providing about 0.01 to about 0.33 moles of the maleic anhydride and/or itaconic anhydride per 1 mole of the amino group of the polyorganosiloxane.

15. The method of claim 12, wherein the maleic anhydride and/or itaconic anhydride reacts with the polyorganosiloxane having an amino group to form a polyorganosiloxane having an α,β-unsaturated carboxy acid amide group.

16. The cross-linked aminosiloxane polymer of claim 3, wherein said second siloxane backbone has the chemical structure:

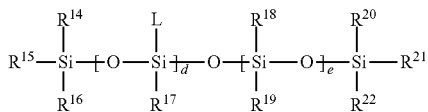

wherein each of $R^{14}$-$R^{22}$ is independently a hydrogen atom, a $C_1$-$C_{12}$ hydrocarbon group, a $C_2$-$C_{30}$ alkenyl group, a $C_6$-$C_{12}$ aromatic group, R'(OR")$_m$, or a polyalkyleneoxy group, where each of R' and R" is independently an alkyl group and "m" is 1 to 3; "d" is from 1 to 100; "e" is from 1 to 3,000; and "L" is said intramolecular structure.

17. The cross-linked aminosiloxane polymer of claim 6, wherein said polyorganosiloxane that has an α,β-unsaturated carboxy acid amide group has one of the following chemical formulas:

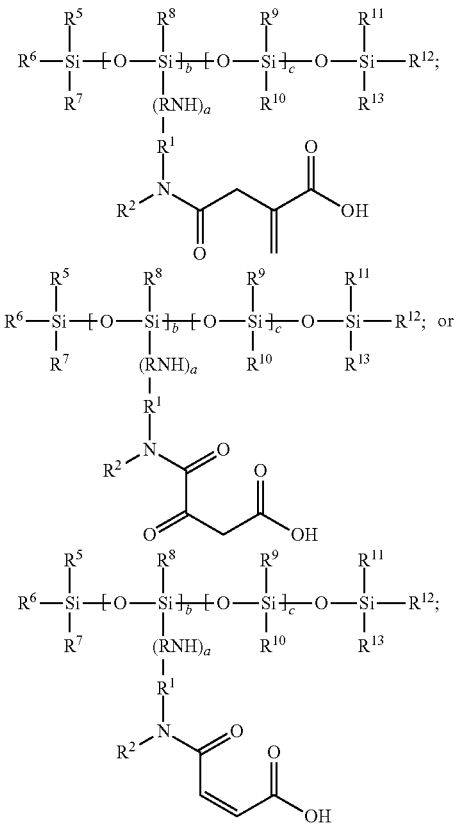

wherein each of R, $R^1$, $R^2$, "a", $R^5$-$R^{13}$, "b", and "c" is as defined above.

18. The cross-linked aminosiloxane polymer of claim 17, wherein said polyorganosiloxane that has an α,β-unsaturated carboxy acid amide group is the reaction product of:
a second polyorganosiloxane having an amino group; and
maleic anhydride and/or itaconic anhydride.

19. The cross-linked aminosiloxane polymer of claim 18, wherein said maleic anhydride and/or said itaconic anhydride reacts in an amount of from about 0.01 to about 0.33 moles per 1 mole of said amino group of said second organopolysiloxane.

20. The method of claim 13, wherein the step of providing the maleic anhydride and/or itaconic anhydride is further defined as providing about 0.01 to about 0.33 moles of the maleic anhydride and/or itaconic anhydride per 1 mole of the amino group of the polyorganosiloxane.

* * * * *

UNITED STATES PATENT AND TRADEMARK OFFICE
CERTIFICATE OF CORRECTION

PATENT NO. : 9,890,253 B2
APPLICATION NO. : 15/311664
DATED : February 13, 2018
INVENTOR(S) : Qian Feng et al.

Page 1 of 2

It is certified that error appears in the above-identified patent and that said Letters Patent is hereby corrected as shown below:

In the Claims

Column 33, Claim 4, Line 10 specifically:

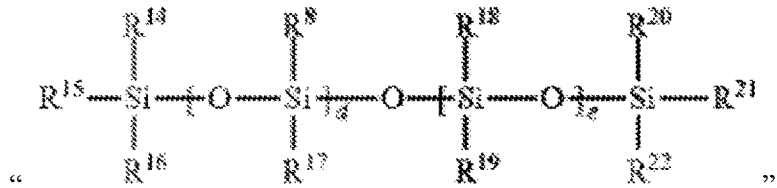

Should be:

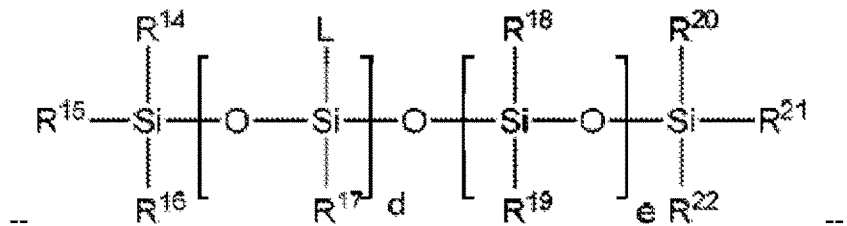

Column 34, Claim 7, Line 10 specifically:

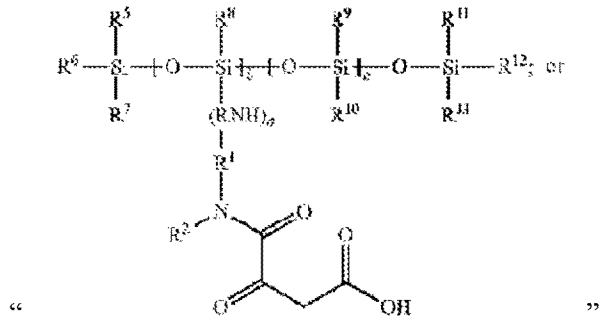

Signed and Sealed this
Second Day of April, 2019

Andrei Iancu
*Director of the United States Patent and Trademark Office*

CERTIFICATE OF CORRECTION (continued)
U.S. Pat. No. 9,890,253 B2

Should be:

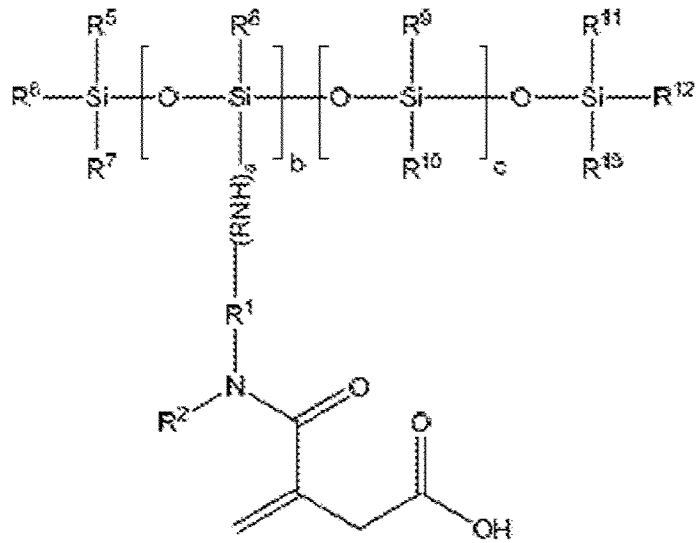

--                                                                                                      --

Column 36, Claim 17, Line 25 specifically:

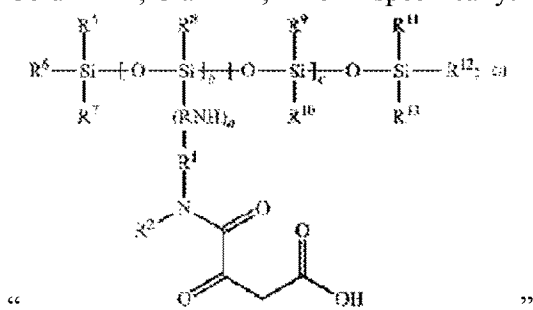

"                                                                                                       "

Should be:

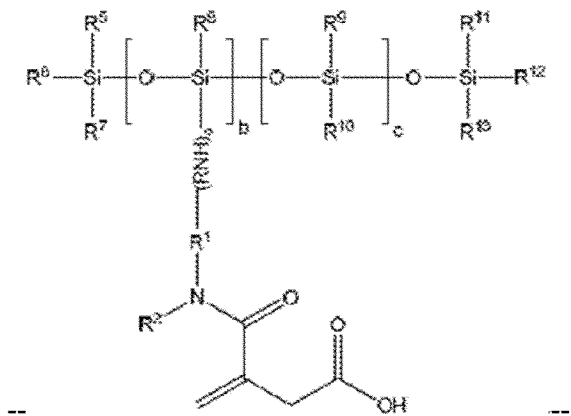

--                                                                                                      --